(12) United States Patent
Silverstone

(10) Patent No.: US 12,049,447 B2
(45) Date of Patent: *Jul. 30, 2024

(54) CRYSTALLINE FORMS OF COMPOSITIONS COMPRISING PSILOCIN AND PSILOCYBIN

(71) Applicant: Zylorion Health Inc., Calgary (CA)

(72) Inventor: Peter Silverstone, Calgary (CA)

(73) Assignee: ZYLORION HEALTH INC., Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/204,870

(22) Filed: Jun. 1, 2023

(65) Prior Publication Data
US 2024/0002338 A1 Jan. 4, 2024

Related U.S. Application Data

(63) Continuation of application No. 17/942,706, filed on Sep. 12, 2022, now Pat. No. 11,667,607.

(60) Provisional application No. 63/357,450, filed on Jun. 30, 2022.

(51) Int. Cl.
*C07D 209/16* (2006.01)

(52) U.S. Cl.
CPC ........ *C07D 209/16* (2013.01); *C07B 2200/13* (2013.01)

(58) Field of Classification Search
CPC .................................................. C07D 209/16
See application file for complete search history.

(56) References Cited

U.S. PATENT DOCUMENTS

| 10,519,175 B2 | 12/2019 | Londesbrough et al. |
| 2019/0119310 A1 | 4/2019 | Londesbrough et al. |

FOREIGN PATENT DOCUMENTS

| CA | 3078765 A1 | 10/2018 |
| WO | WO 2022123232 A1 | 6/2022 |

OTHER PUBLICATIONS

PCT International Search Report and Written Opinion in International Application No. PCT/IB2023/000312, dated Oct. 25, 2023, 9 pages.
Coelho et al., "Condensin-Dependent Localisation of Topoisomerase II to an Axial Chromosomal Structure is Required for Sister Chromatid Resolution during Mitosis," *J. Cell Sci.* (2003), 116:4763-4776, The Company of Biologists Ltd.
Coelho and Kern, "Discussion of the Indexing Algorithms within TOPAS," *IUCr Commission on Powder Diffraction Newsletter* (2003). 32:43-45.

*Primary Examiner* — Shawquia Jackson
(74) *Attorney, Agent, or Firm* — DLA Piper LLP (US)

(57) ABSTRACT

The present disclosure provides a composition comprising crystalline forms A, B, and C of psilocin and psilocybin. Solvent screen, X-ray powder diffractogram, thermogravimetric mass spectroscopy, differential scanning calorimetry, $^1$H-NMR, dynamic vapor sorption, and UPLC data on each of the crystalline forms is presented, along with methods preparing each of the crystalline forms.

15 Claims, 22 Drawing Sheets

CRYSTALLINE FORMS OF COMPOSITIONS COMPRISING PSILOCIN AND PSILOCYBIN

CROSS-REFERENCE TO RELATED APPLICATIONS

This application is a continuation application of U.S. application Ser. No. 17/942,706 filed Sep. 12, 2022, now issued as U.S. Pat. No. 11,667,607; which claims the benefit under 35 USC § 119(e) to U.S. Application Ser. No. 63/357,450 filed Jun. 30, 2022. The disclosure of each of the prior applications is considered part of and is incorporated by reference in the disclosure of this application.

BACKGROUND OF THE INVENTION

Field of the Invention

This invention is directed to crystalline forms of a compound of psilocybin and psilocin and uses of the compounds in the treatment of mental health disorders and/or other central nervous system conditions and disorders.

Background Information

Various natural plants and fungi contain psychedelic compounds which cause individuals to experience hallucinogenic or similar experiences. Among the most common type of naturally occurring psychedelics is psilocybin, of which has been found in over 180 species of mushrooms. Psilocybin-containing mushrooms also have other psychedelic compounds, the most abundant of which is its primary metabolite, psilocin. Psilocybin is metabolized in the gastrointestinal system, primarily to psilocin, which is then absorbed and causes the psychedelic effects.

These psychedelic effects are dose-dependent and usually include changes in visual, auditory, and cognitive experiences. These psilocybin experiences may occur because psilocybin is similar in structure to the neurotransmitter serotonin (5-hydroxytryptamine, 5-HT), and binds to a 5-HT receptor.

In contrast to psilocybin, psilocin is chemically unstable and rapidly oxidizes when exposed to air. For this reason, there have been very few clinical or research studies on the impact of psilocin given alone or comparison to psilocybin. It is proposed that psilocin has a faster absorption and a more rapid onset of action. Psilocin binds to different receptors than psilocybin and as such has a different range of actions.

Because of the different properties of psilocybin and psilocin, a compound which combines both psilocybin and psilocin may be expected to have unique and beneficial properties both compared to either compound alone but also to co-administration of the compounds.

It has been suggested that psychedelics such as psilocybin and psilocin may be useful in treating certain mental health disorders and central nervous system disorders. This is thought to be especially true for disorders that are resistant to currently available treatments such as post-traumatic stress disorder and treatment resistant depression.

There is a need for new treatments for wide variety of mental health disorders and central nervous system disorders. One such treatment may be a crystalline form of psilocybin and psilocin, especially for use in disorders resistant to current treatments.

SUMMARY OF THE INVENTION

The present disclosure provides several novel compositions comprising a crystalline form of psilocin and psilocybin:

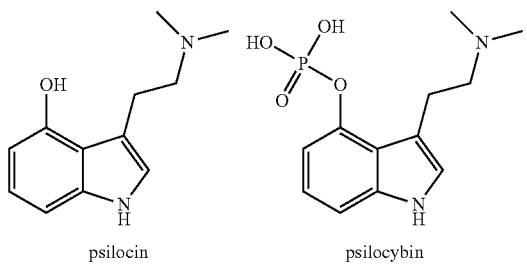

psilocin    psilocybin

Described and identified herein as crystalline Forms A, B, and C. Crystalline Form A may be characterized by a XRPD pattern comprising a significant peak at a 2θ angle of about 10.1°. A XRPD pattern of crystalline Form A may additionally comprise a significant peak at 2θ angle of about 19.16°. A XRPD pattern of crystalline Form A may additionally comprise significant peaks at 2θ angles of about 10.74°, about 25.3°, and about 24.07°. Yet further, a XRPD pattern of crystalline Form A may additionally comprise significant peaks at 2θ angles of about 14.54°, about 16.5°, about 13.44°, about 23.42°, and about 8.62°. Crystalline Form B may be characterized by a XRPD pattern comprising a significant peak at a 2θ angle of about 18.54°. A XRPD pattern of crystalline Form B may additionally comprise a significant peak at 2θ angle of about 8.54°. A XRPD pattern of crystalline Form B may additionally comprise significant peaks at 2θ angles of about 22.78°, about 14.27°, and about 21.12°. Yet further, a XRPD pattern of crystalline Form B may additionally comprise significant peaks at 2θ angles of about 14.12°, about 10.05°, about 9.94°, about 24.94°, and about 25.02°. Crystalline Form C may be characterized by a XRPD pattern comprising a significant peak at a 2θ angle of about 9.18°. A XRPD pattern of crystalline Form C may additionally comprise a significant peak at 2θ angle of about 17.95°. A XRPD pattern of crystalline Form C may additionally comprise significant peaks at 2θ angles of about 10.42°, about 24.22°, and about 18.38°. Yet further, a XRPD pattern of crystalline Form C may additionally comprise significant peaks at 2θ angles of about 19.82°, about 17.46°, about 14.82°, about 22.38°, and about 14.06°.

In one embodiment, the present application provides pharmaceutical composition comprising a crystalline form of psilocin and psilocybin and a pharmaceutically acceptable excipient. In one embodiment the crystalline form is crystalline Form A, crystalline Form B or From C. In one embodiment, crystalline Form A is characterized by a XRPD pattern comprising a significant peak at a 2θ angle of about 10.1°; the XRPD pattern further comprises a significant peak at a 2θ angle of about 19.16°; at a 2θ angles of about 10.74°, about 25.3°, and about 24.07°; and/or the XRPD pattern further comprises a significant peak at a 2θ angles of about 14.54°, about 16.5°, about 13.44°, about 23.42°, and about 8.62°. In one embodiment, crystalline Form A has a ratio of psilocybin to psilocin of about 1:1. In one embodiment, crystalline Form A has a chemical purity of about 95% or greater. In some embodiments, crystalline Form A contains not more than about 5 mol % of other solid forms. In some embodiments, the composition of crystalline Form A of psilocin and psilocybin comprises about 95 mol % crystalline Form A, about 2.5 mol % psilocin, and about 2.5 mol % psilocybin. In one embodiment, crystalline Form A is a co-crystal formed between psilocin and psilocybin. In one embodiment, crystalline Form A is a salt formed between psilocin and psilocybin.

In one embodiment, crystalline Form B is characterized by a XRPD pattern comprising a significant peak at a 2θ angle of about 18.54°; the XRPD pattern further comprises a significant peak at a 2θ angle of about 8.54°; the XRPD pattern further comprises a significant peak at a 2θ angles of about 22.78°, about 14.27°, and about 21.120 and/or the XRPD pattern further comprises a significant peak at a 2θ angles of about 14.12°, about 10.05°, about 9.94°, about 24.94°, and about 25.02°. In one embodiment, crystalline Form B has ratio of psilocybin to psilocin of about 1.3:1. In one embodiment, crystalline Form B has ratio of psilocybin to psilocin of about 1:1. In one embodiment, crystalline Form B has a chemical purity of about 95% or greater. In some embodiments, crystalline Form B contains not more than about 5 mol % of other solid forms. In some embodiments, the composition of crystalline Form B of psilocin and psilocybin comprises about 95 mol % crystalline Form B, about 2.5 mol % psilocin, and about 2.5 mol % psilocybin. In one embodiment, crystalline Form B is a co-crystal formed between psilocin and psilocybin. In one embodiment, crystalline Form B is a salt formed between psilocin and psilocybin.

In one embodiment, crystalline Form C is characterized by a XRPD pattern comprising a significant peak at a 2θ angle of about 9.18°; the XRPD pattern further comprises a significant peak at a 2θ angle of about 17.95°; the XRPD pattern further comprises a significant peak at a 2θ angles of about 10.42°, about 24.22°, and about 18.38°; and/or the XRPD pattern further comprises a significant peak at a 2θ angles of about 19.82°, about 17.46°, about 14.82°, about 22.38°, and about 14.06°. In one embodiment, crystalline Form C has ratio of psilocybin to psilocin of about 1:1. In one embodiment, crystalline Form C has a chemical purity of about 95% or greater. In some embodiments, crystalline Form C contains not more than about 5 mol % of other solid forms. In some embodiments, the composition of crystalline Form C of psilocin and psilocybin comprises about 95 mol % crystalline Form C, about 2.5 mol % psilocin, and about 2.5 mol % psilocybin. In one embodiment, crystalline Form C is a co-crystal formed between psilocin and psilocybin. In one embodiment, crystalline Form C is a salt formed between psilocin and psilocybin.

In one embodiment, the present invention provides a method of treating or ameliorating a disease or disorder by administering to a subject a composition comprising a crystalline form of psilocin and psilocybin thereby treating the disease or disorder In one embodiment, the disease or disorder is a mental health disorder or a central nervous system (CNS) disorder. In one embodiment, the mental health disorder is selected from depressive disorders, anxiety disorders, post-traumatic stress disorder and addiction disorders. In one embodiment, the CNS disorder is selected from chronic pain disorders and cognitive disorders.

In one embodiment the crystalline form is crystalline Form A, crystalline Form B or From C. In one embodiment, crystalline Form A is characterized by a XRPD pattern comprising a significant peak at a 2θ angle of about 10.1°; the XRPD pattern further comprises a significant peak at a 2θ angle of about 19.16°; at a 2θ angles of about 10.74°, about 25.3°, and about 24.07°; and/or the XRPD pattern further comprises a significant peak at a 2θ angles of about 14.54°, about 16.5°, about 13.44°, about 23.42°, and about 8.62°. In one embodiment, crystalline Form A has a ratio of psilocybin to psilocin of about 1:1. In one embodiment, crystalline Form A has a chemical purity of about 95% or greater. In some embodiments, crystalline Form A contains not more than about 5 mol % of other solid forms. In some embodiments, the composition of crystalline Form A of psilocin and psilocybin comprises about 95 mol % crystalline Form A, about 2.5 mol % psilocin, and about 2.5 mol % psilocybin. In one embodiment, crystalline Form A is a co-crystal formed between psilocin and psilocybin. In one embodiment, crystalline Form A is a salt formed between psilocin and psilocybin.

In one embodiment, crystalline Form B is characterized by a XRPD pattern comprising a significant peak at a 2θ angle of about 18.54°; the XRPD pattern further comprises a significant peak at a 2θ angle of about 8.54°; the XRPD pattern further comprises a significant peak at a 2θ angles of about 22.78°, about 14.27°, and about 21.12° and/or the XRPD pattern further comprises a significant peak at a 2θ angles of about 14.12°, about 10.05°, about 9.94°, about 24.94°, and about 25.02°. In one embodiment, crystalline Form B has ratio of psilocybin to psilocin of about 1.3:1. In one embodiment, crystalline Form B has ratio of psilocybin to psilocin of about 1:1. In one embodiment, crystalline Form B has a chemical purity of about 95% or greater. In some embodiments, crystalline Form B contains not more than about 5 mol % of other solid forms. In some embodiments, the composition of crystalline Form B of psilocin and psilocybin comprises about 95 mol % crystalline Form B, about 2.5 mol % psilocin, and about 2.5 mol % psilocybin. In one embodiment, crystalline Form B is a co-crystal formed between psilocin and psilocybin. In one embodiment, crystalline Form B is a salt formed between psilocin and psilocybin.

In one embodiment, crystalline Form C is characterized by a XRPD pattern comprising a significant peak at a 2θ angle of about 9.18°; the XRPD pattern further comprises a significant peak at a 2θ angle of about 17.95°; the XRPD pattern further comprises a significant peak at a 2θ angles of about 10.42°, about 24.22°, and about 18.38°; and/or the XRPD pattern further comprises a significant peak at a 2θ angles of about 19.82°, about 17.46°, about 14.82°, about 22.38°, and about 14.06°. In one embodiment, crystalline Form C has ratio of psilocybin to psilocin of about 1:1. In one embodiment, crystalline Form C has a chemical purity of about 95% or greater. In some embodiments, crystalline Form C contains not more than about 5 mol % of other solid forms. In some embodiments, the composition of crystalline Form C of psilocin and psilocybin comprises about 95 mol % crystalline Form C, about 2.5 mol % psilocin, and about 2.5 mol % psilocybin. In one embodiment, crystalline Form C is a co-crystal formed between psilocin and psilocybin. In one embodiment, crystalline Form C is a salt formed between psilocin and psilocybin.

DETAILED DESCRIPTION OF THE INVENTION

Figure 1:
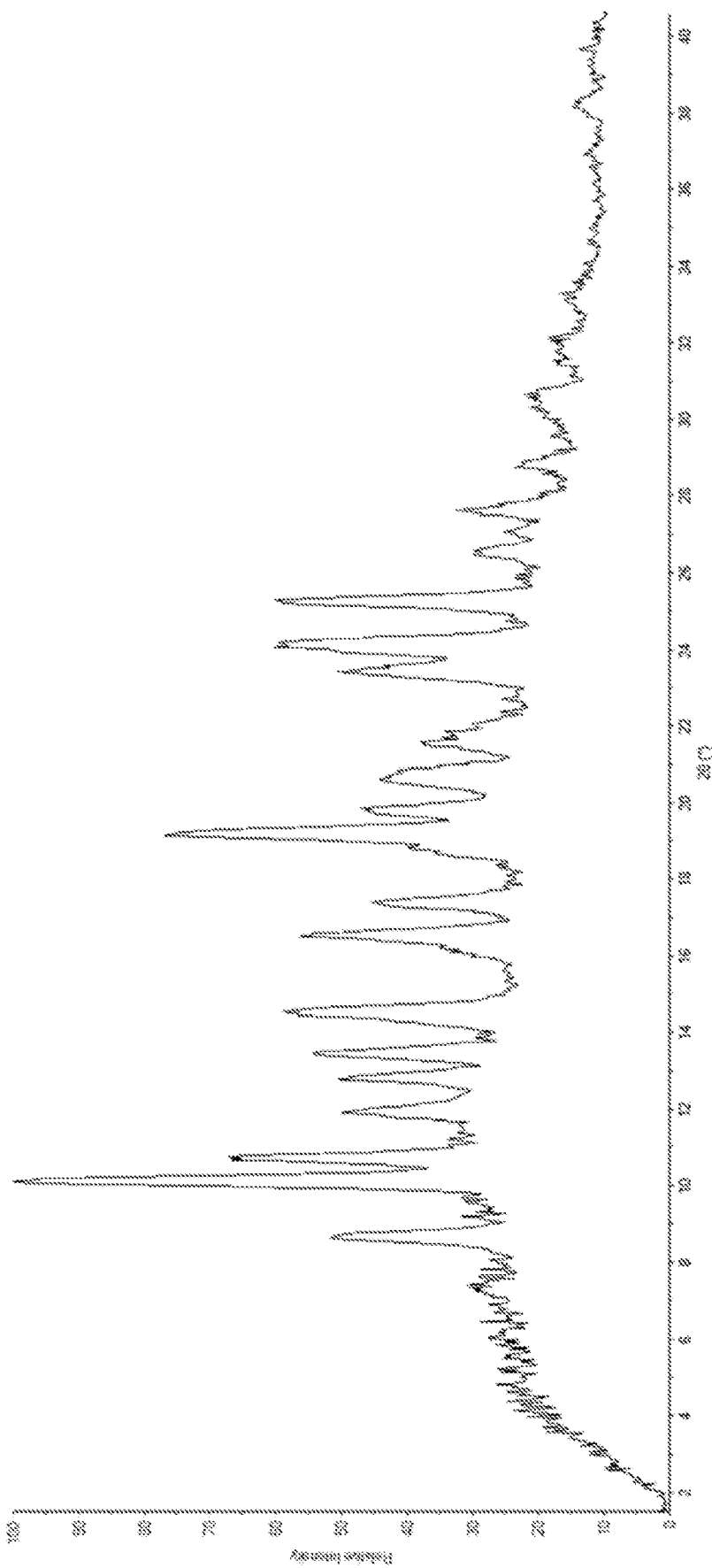
FIG. 1 shows an X-ray powder diffractogram (XRPD) plot of crystalline Form A.

The present invention is based on the seminal discovery that psilocybin and psilocin form crystalline forms and specifically, that crystalline forms of a composition comprising psilocybin and psilocin may be useful for treating certain mental health disorders and central nervous system disorders.

Before the present compositions and methods are described, it is to be understood that this invention is not limited to the particular processes, formulations, compositions, or methodologies described, as these may vary. It is also to be understood that the terminology used in the description is for the purpose of describing the particular versions or embodiments only and is not intended to limit the scope of embodiments herein which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of embodiments herein, the preferred methods, devices, and materials are now described. All publications mentioned herein are incorporated by reference in their entirety. Nothing herein is to be construed as an admission that embodiments herein are not entitled to antedate such disclosure by virtue of prior invention.

It must also be noted that as used herein and in the appended claims, the singular forms "a," "an," and "the" include plural reference unless the context clearly dictates otherwise.

The transitional term "comprising," which is synonymous with "including," "containing," or "characterized by," is inclusive or open-ended and does not exclude additional, unrecited elements or method steps.

As used herein, the term "consists of" or "consisting of" means that the composition, formulation or the method includes only the elements, steps, or ingredients specifically recited in the particular claimed embodiment or claim.

As used herein, the term "consisting essentially of" or "consists essentially of" means that the composition, formulation or the method includes only the elements, steps or ingredients specifically recited in the particular claimed embodiment or claim and may optionally include additional elements, steps or ingredients that do not materially affect the basic and novel characteristics of the particular embodiment or claim. For example, the only active ingredient(s) in the formulation or method that treats the specified condition (e.g., nutrient depletion) is the specifically recited therapeutic(s) in the particular embodiment or claim.

As used herein, two embodiments are "mutually exclusive" when one is defined to be something which is different from the other.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 1° C. to 3° C.," which is intended to include 1° C., 3° C., and everything in between to any number of significant figures (e.g., 1.255° C., 2.1° C., 2.9999° C., etc.).

As used herein, the term "about" means plus or minus 10% of the numerical value of the number with which it is being used. Therefore, about 50% means in the range of 45% to 55%. For example, "about 100° C." means a temperature in the range of 90° C. to 110° C. For example, "a 2θ angle of about 10°" means a 2θ angle in the range of 9° to 11°.

The term "substantially free" or as used herein, alone or in combination, and is used interchangeably with, the term "substantially pure", refers to a compound which is free from all other compounds within the limits of detection as measured by any means including nuclear magnetic resonance (NMR), gas chromatography/mass spectroscopy (GC/MS), or liquid chromatography/mass spectroscopy (LC/MS). In embodiments, substantially free may be less than about 1.0%, less than about 0.5%, less than about 0.4%, less than about 0.3%, less than about 0.2%, less than about 0.1%, less than about 0.05%, or less than about 0.01%.

Crystalline Forms

The present disclosure includes embodiments directed to a composition comprising a crystalline form of psilocin and psilocybin:

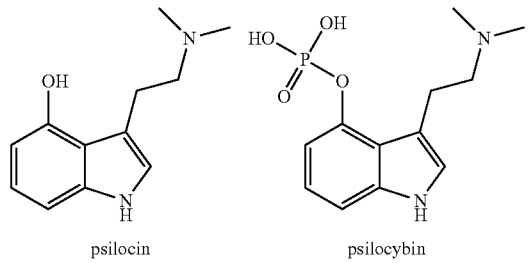

psilocin            psilocybin

In some embodiments, the crystalline form of the composition comprising psilocin and psilocybin is crystalline Form A.

In some embodiments, crystalline Form A is characterized by a XRPD pattern comprising a significant peak at a 2θ angle of about 10.1°. In some embodiments, the XRPD pattern of crystalline Form A may additionally comprise a significant peak at 2θ angle of about 19.16°. In some embodiments, the XRPD pattern of crystalline Form A may additionally comprise significant peaks at 2θ angles of about 10.74°, about 25.3°, and about 24.07°. In some embodiments, the XRPD pattern of crystalline Form A may additionally comprise significant peaks at 2θ angles of about 14.54°, about 16.5°, about 13.44°, about 23.42°, and about 8.62°. In some embodiments, crystalline Form A is characterized by an XRPD pattern of FIG. 1.

Figure 4:
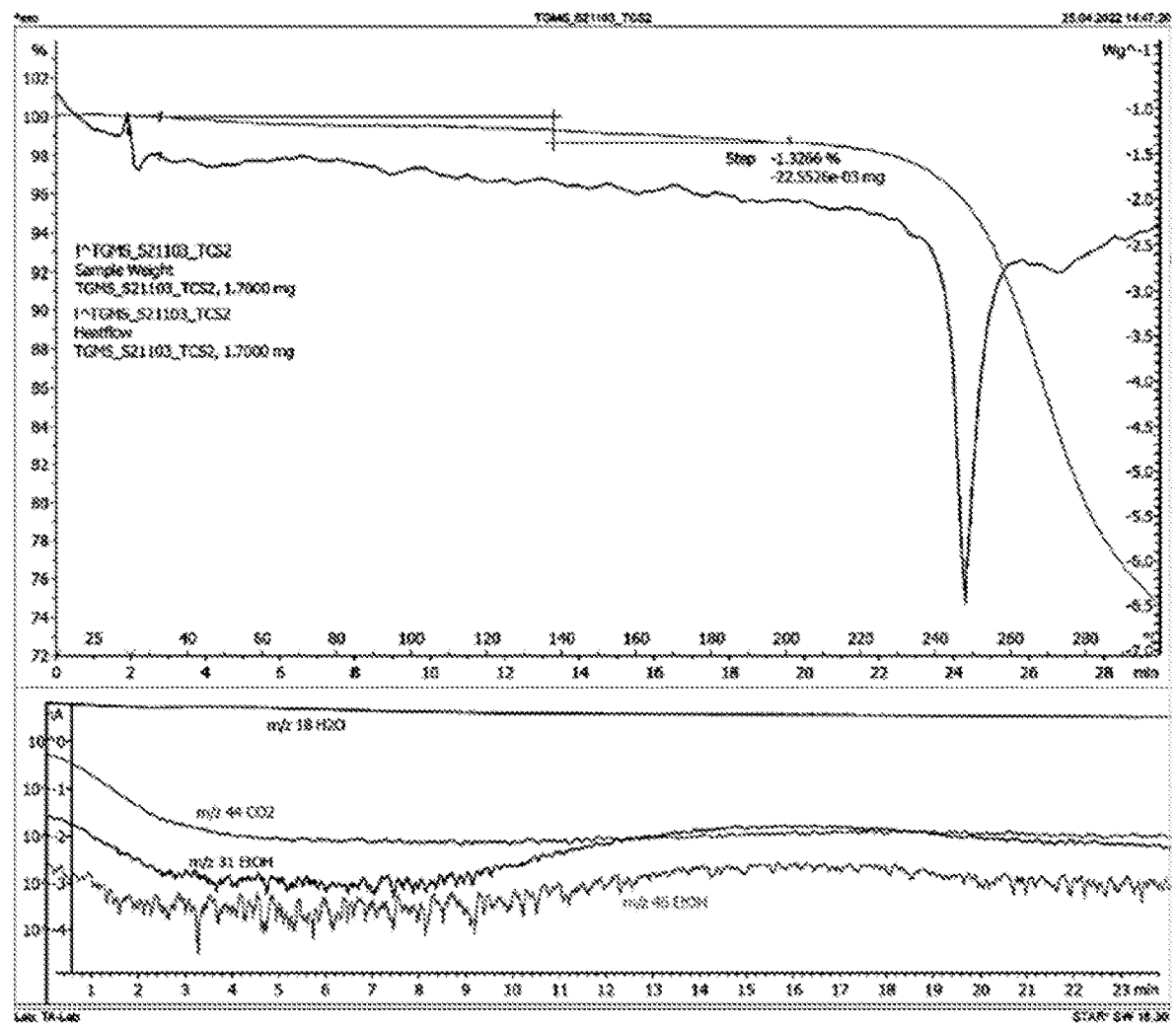
FIG. 4 shows the thermogravimetric mass spectroscopy (TGMS) thermogram plot of crystalline Form A.

In one embodiment, crystalline Form A has a TGMS thermograph corresponding substantially to the representative TGMS thermogram as depicted in FIG. 4. In some embodiments, negligible weight loss is observed. Weight loss (1.3%) is observed between 40-200° C. by TGMS for crystalline Form A.

Figure 5:
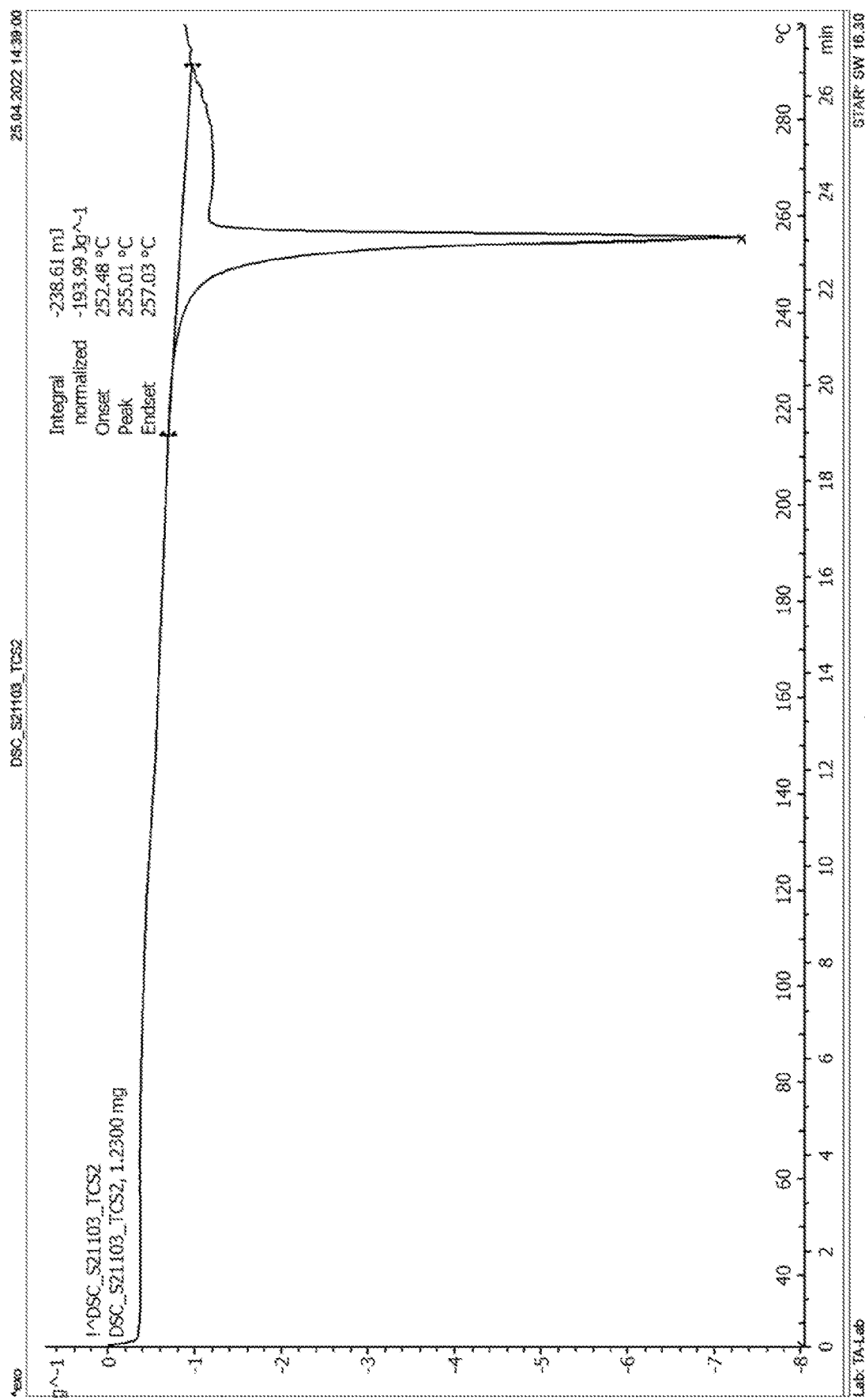
FIG. 5 shows the differential scanning calorimetry (DSC) thermogram plot of crystalline Form A.

In one embodiment, crystalline Form A has a DSC thermogram corresponding substantially as depicted in FIG. 5. In certain embodiments, crystalline Form A is characterized by a DSC plot comprising a sharp endothermic event at a temperature of about 255° C.

In some embodiments, crystalline Form A has ratio of psilocybin to psilocin of about 1:1, about 1.1:1, about 1.2:1, about 1.3:1, about 1.4:1, about 1.5:1, about 1.6:1, about 1.7:1, about 1.8:1, about 1.9:1, about 2:1, about 1:1.1, about 1:1.2, about 1:1.3, about 1:1.4, about 1:1.5, about 1:1.6, about 1:1.7, about 1:1.8, about 1:1.9, or about 1:2. In some embodiments, crystalline Form A has ratio of psilocybin to psilocin of about 1:1.

In some embodiments, crystalline Form A has a chemical purity of about 95% or greater, is about 96% or greater, is about 97% or greater, is about 98% or greater, is about 98.5% or greater, is about 99% or greater, is about 99.5% or greater, or is about 99.8% or greater. In some embodiments, crystalline Form A is substantially pure.

In some embodiments, crystalline Form A contains not more than about 0.01 mol %, about 0.02 mol %, about 0.03 mol %, about 0.04 mol %, about 0.05 mol %, about 0.06 mol %, about 0.07 mol %, about 0.08 mol %, about 0.09 mol %, about 0.1 mol %, about 0.15 mol %, about 0.2 mol %, about 0.25 mol %, about 0.3 mol %, about 0.35 mol %, about 0.4 mol %, about 0.45 mol %, about 0.5 mol %, about 0.55 mol %, about 0.6 mol %, about 0.65 mol %, about 0.7 mol %, about 0.75 mol %, about 0.8 mol %, about 0.85 mol %, about 0.9 mol %, about 0.95 mol %, about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, about 20 mol %, of other solid forms, e.g., amorphous form. In some embodiments, crystalline Form A of is substantially free of other solid forms.

In some embodiments, the composition of crystalline Form A of psilocin and psilocybin comprises about 99 mol % crystalline Form A, about 0.5 mol % psilocin, and about 0.5 mol % psilocybin; about 98 mol % crystalline Form A, about 1.0 mol % psilocin, and about 1.0 mol % psilocybin; about 97 mol % crystalline Form A, about 1.5 mol % psilocin, and about 1.5 mol % psilocybin; about 96 mol % crystalline Form A, about 2.0 mol % psilocin, and about 2.0 mol % psilocybin; about 95 mol % crystalline Form A, about 2.5 mol % psilocin, and about 2.5 mol % psilocybin; about 94 mol % crystalline Form A, about 3.0 mol % psilocin, and about 3.0 mol % psilocybin; about 93 mol % crystalline Form A, about 3.5 mol % psilocin, and about 3.5 mol % psilocybin; about 92 mol % crystalline Form A, about 4.0 mol % psilocin, and about 4.0 mol % psilocybin; about 91 mol % crystalline Form A, about 4.5 mol % psilocin, and about 4.5 mol % psilocybin; or about 90 mol % crystalline Form A, about 5.0 mol % psilocin, and about 5.0 mol % psilocybin.

In some embodiments, crystalline Form A is anhydrous.

In some embodiments, crystalline Form A is a salt formed between psilocin and psilocybin.

In some embodiments, crystalline Form A is a co-crystal formed between psilocin and psilocybin.

Some embodiments are directed to a composition comprising a crystalline form of psilocin and psilocybin:

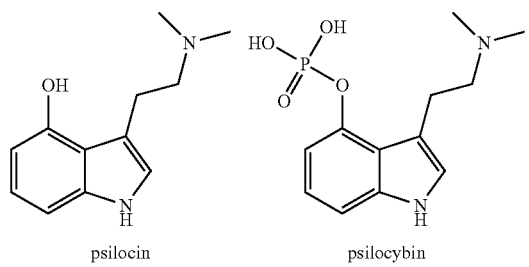

wherein crystalline Form A is characterized by unit cell parameters which are substantially equal to the following:

Unit cell dimensions:
a=9.3674(3) Å
b=11.2660(6) Å
c=24.2741(9) Å
α=90 degrees
β=90 degrees
γ=90 degrees
Space group=P2$_1$2$_1$2$_1$
Molecules/asymmetric unit=1

In some embodiments, the unit cell parameters were measured about 296K.

In some embodiments, crystalline Form A has a geometry of hydrogen bonds substantially as listed in Table A.

TABLE A

| D-H...A | D-H [Å] | H...A [Å] | D...A [Å] | D-H...A [°] |
|---|---|---|---|---|
| O1-H1...N23$^i$ | 0.88(2) | 1.60(2) | 2.46(2) | 162(2) |
| N11-H11...O3$^{ii}$ | 0.96(5) | 2.17(4) | 2.97(4) | 140(6) |
| N17-H17...O2$^{iii}$ | 0.85(7) | 1.83(7) | 2.59(6) | 147(8) |
| N28-H28...O1$^{iv}$ | 0.87(7) | 2.32(6) | 3.13(5) | 153(10) |
| O34-H34...O3$^v$ | 0.88(10) | 1.69(8) | 2.49(7) | 151(5) |

In some embodiments, crystalline Form A has atomic coordinates of non-hydrogen atoms substantially as listed in Table B.

TABLE B

| | x | y | z | U(eq) |
|---|---|---|---|---|
| O1 | 0.1251(14) | 0.0326(16) | 0.4198(4) | 0.0253 |
| O2 | 0.077(3) | 0.0094(13) | 0.3153(5) | 0.0253 |
| O3 | 0.190(3) | 0.190(2) | 0.3483(6) | 0.0253 |
| P4 | 0.0916(7) | 0.0915(7) | 0.3636(3) | 0.0253 |
| O5 | −0.054(2) | 0.157(3) | 0.3724(5) | 0.0253 |
| C6 | −0.1818(8) | 0.102(5) | 0.3771(8) | 0.0253 |
| C7 | −0.221(2) | 0.009(6) | 0.4089(13) | 0.0253 |

TABLE B-continued

| | x | y | z | U(eq) |
|---|---|---|---|---|
| C8 | −0.357(3) | −0.030(9) | 0.4084(19) | 0.0253 |
| C9 | −0.466(2) | 0.022(11) | 0.375(2) | 0.0253 |
| C10 | −0.4261(9) | 0.116(10) | 0.3436(15) | 0.0253 |
| N11 | −0.512(3) | 0.188(12) | 0.3068(16) | 0.0253 |
| C12 | −0.386(5) | 0.277(10) | 0.2836(13) | 0.0253 |
| C13 | −0.265(4) | 0.250(7) | 0.3069(10) | 0.0253 |
| C14 | −0.2791(18) | 0.156(7) | 0.3445(10) | 0.0253 |
| C15 | −0.139(6) | 0.313(5) | 0.2890(13) | 0.0253 |
| C16 | −0.082(4) | 0.261(6) | 0.2343(10) | 0.0253 |
| N17 | 0.054(6) | 0.324(5) | 0.2219(15) | 0.0253 |
| C18 | 0.140(5) | 0.246(6) | 0.1809(13) | 0.0253 |
| C19 | 0.146(7) | 0.370(3) | 0.269(2) | 0.0253 |
| C21 | 0.8842(18) | 0.5884(19) | 0.9383(6) | 0.0253 |
| C22 | 0.7490(17) | 0.7295(10) | 0.9827(10) | 0.0253 |
| N23 | 0.8087(12) | 0.6116(8) | 0.9893(5) | 0.0253 |
| C24 | 0.7012(15) | 0.5244(13) | 1.0037(8) | 0.0253 |
| C25 | 0.591(2) | 0.533(3) | 0.9591(11) | 0.0253 |
| C26 | 0.508(4) | 0.422(3) | 0.9490(17) | 0.0253 |
| C27 | 0.543(5) | 0.306(3) | 0.963(2) | 0.0253 |
| N28 | 0.435(7) | 0.236(4) | 0.942(3) | 0.0253 |
| C29 | 0.337(7) | 0.302(6) | 0.917(3) | 0.0253 |
| C30 | 0.212(8) | 0.268(7) | 0.891(3) | 0.0253 |
| C31 | 0.124(7) | 0.356(9) | 0.868(3) | 0.0253 |
| C32 | 0.161(6) | 0.474(8) | 0.872(3) | 0.0253 |
| C33 | 0.292(5) | 0.508(6) | 0.899(3) | 0.0253 |
| O34 | 0.330(4) | 0.628(6) | 0.906(3) | 0.0253 |
| C35 | 0.379(5) | 0.422(5) | 0.920(2) | 0.0253 |

In some embodiments, crystalline Form A has atomic coordinates of hydrogen atoms substantially as listed in Table C.

TABLE C

| | x | y | z | U(eq) |
|---|---|---|---|---|
| H1 | 0.1396(11) | 0.074(2) | 0.4502(3) | 0.0253 |
| H7 | −0.151(3) | −0.029(5) | 0.4319(14) | 0.0253 |
| H8 | −0.379(5) | −0.097(9) | 0.431(2) | 0.0253 |
| H9 | −0.563(3) | −0.005(13) | 0.374(2) | 0.0253 |
| H11 | −0.612(2) | 0.172(14) | 0.3030(19) | 0.0253 |
| H12 | −0.389(6) | 0.337(10) | 0.2556(15) | 0.0253 |
| H15A | −0.075(5) | 0.294(4) | 0.3185(12) | 0.0253 |
| H15B | −0.147(8) | 0.398(5) | 0.2858(18) | 0.0253 |
| H16A | −0.146(5) | 0.280(7) | 0.2048(11) | 0.0253 |
| H16B | −0.074(3) | 0.176(5) | 0.2375(8) | 0.0253 |
| H17 | 0.041(8) | 0.386(5) | 0.2026(19) | 0.0253 |
| H18A | 0.205(4) | 0.181(6) | 0.1844(12) | 0.0253 |
| H18B | 0.203(6) | 0.295(7) | 0.1601(17) | 0.0253 |
| H18C | 0.075(4) | 0.206(7) | 0.1563(10) | 0.0253 |
| H19A | 0.213(7) | 0.336(3) | 0.2941(19) | 0.0253 |
| H19B | 0.086(8) | 0.405(2) | 0.296(2) | 0.0253 |
| H19C | 0.211(9) | 0.429(4) | 0.255(2) | 0.0253 |
| H21A | 0.951(2) | 0.627(3) | 0.9141(7) | 0.0253 |
| H21B | 0.817(3) | 0.575(3) | 0.9093(5) | 0.0253 |
| H21C | 0.944(2) | 0.520(2) | 0.9427(10) | 0.0253 |
| H22A | 0.778(2) | 0.8072(10) | 0.9708(14) | 0.0253 |
| H22B | 0.715(2) | 0.7579(14) | 1.0176(12) | 0.0253 |
| H22C | 0.6710(17) | 0.7266(10) | 0.9571(11) | 0.0253 |
| H24A | 0.6599(17) | 0.542(2) | 1.0390(8) | 0.0253 |
| H24B | 0.742(2) | 0.4463(11) | 1.0054(11) | 0.0253 |
| H25A | 0.635(3) | 0.565(3) | 0.9267(9) | 0.0253 |
| H25B | 0.5179(14) | 0.587(3) | 0.9706(16) | 0.0253 |
| H27 | 0.629(5) | 0.2905(18) | 0.984(3) | 0.0253 |
| H28 | 0.436(8) | 0.159(4) | 0.946(4) | 0.0253 |
| H30 | 0.186(9) | 0.185(8 | 0.890(4) | 0.0253 |
| H31 | 0.037(8) | 0.334(10) | 0.851(4) | 0.0253 |
| H32 | 0.100(6) | 0.533(9) | 0.856(4) | 0.0253 |
| H34 | 0.294(4) | 0.682(7) | 0.884(3) | 0.0253 |

In some embodiments, the crystalline form of the composition comprising psilocin and psilocybin is crystalline Form B.

In some embodiments, crystalline Form B is characterized by a XRPD pattern comprising a significant peak at a 2θ angle of about 18.54°. In some embodiments, crystalline Form B is characterized by a XRPD pattern of crystalline Form B may additionally comprise a significant peak at 2θ angle of about 8.54°. In some embodiments, crystalline Form B is characterized by a XRPD pattern of crystalline Form B may additionally comprise significant peaks at 2θ angles of about 22.78°, about 14.27°, and about 21.12°. In some embodiments, crystalline Form B is characterized by a XRPD pattern of crystalline Form B may additionally comprise significant peaks at 2θ angles of about 14.12°, about 10.05°, about 9.94°, about 24.94°, and about 25.02°. In some embodiments, crystalline Form B is characterized by an XRPD pattern of FIG. 2.

Figure 6:
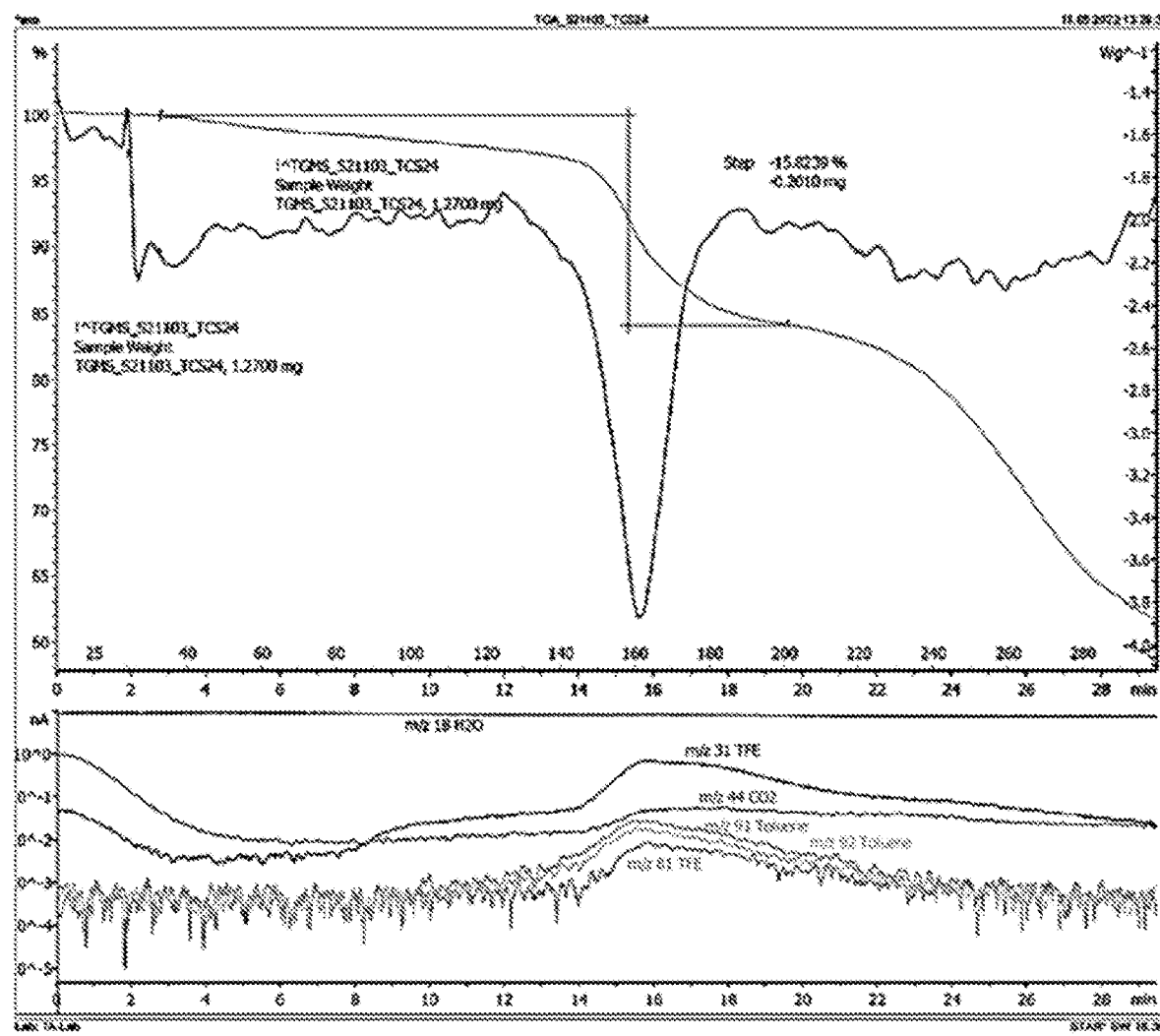
FIG. 6 shows the TGMS thermogram plot of crystalline Form B.

In one embodiment, crystalline Form B has a TGMS thermograph corresponding substantially to the representative TGMS thermogram as depicted in FIG. 6. In some embodiments, negligible weight loss is observed. Weight loss (15.8%) is observed between 40-200° C. by TGMS for crystalline Form B.

Figure 7:
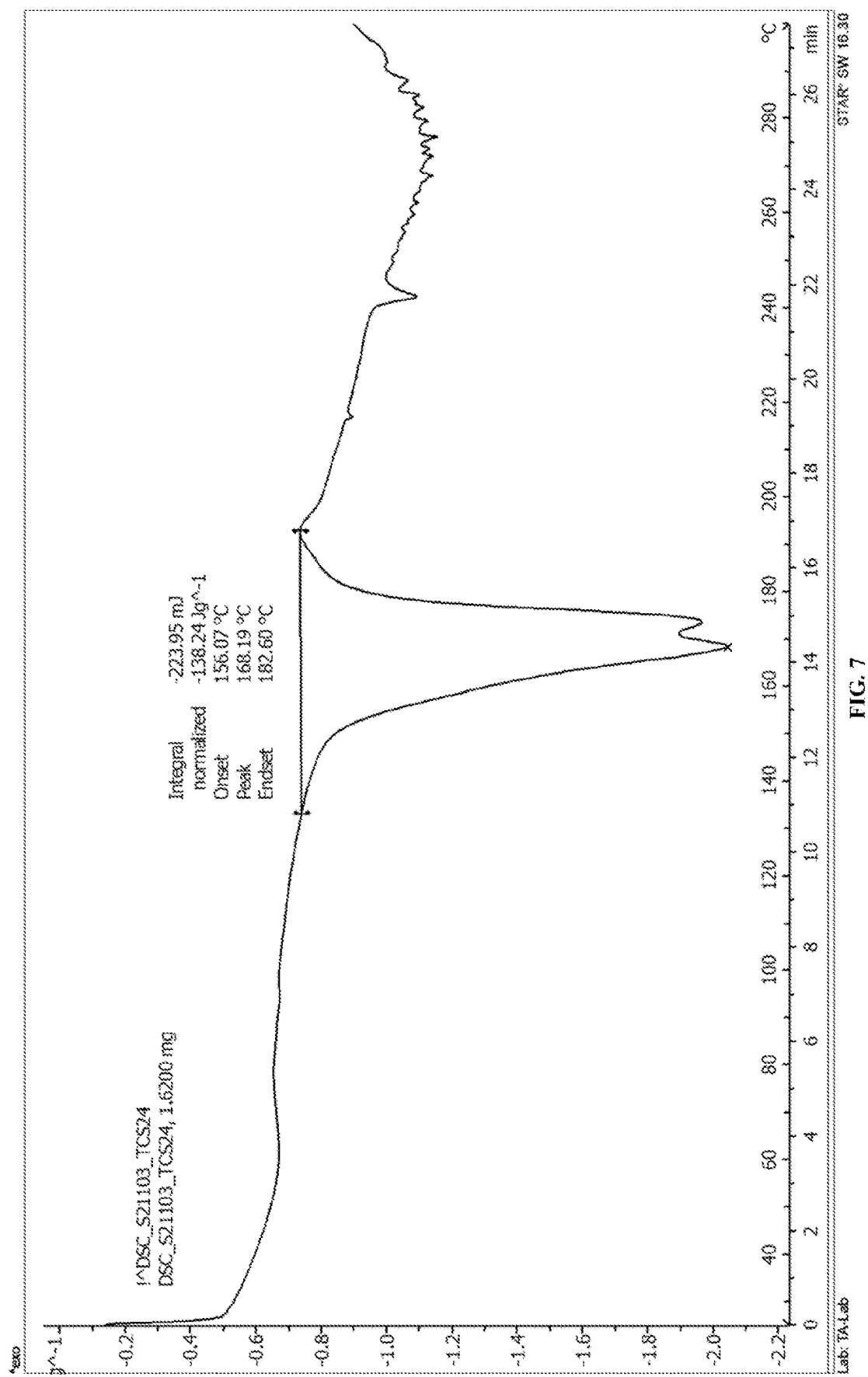
FIG. 7 shows the DSC thermogram plot of crystalline Form B.

In one embodiment, crystalline Form B has a DSC thermogram corresponding substantially as depicted in FIG. 7. In certain embodiments, crystalline Form B is characterized by a DSC plot comprising a broad endothermic event at a temperature of about 168.2° C.

In some embodiments, crystalline Form B has ratio of psilocybin to psilocin of about 1:1, about 1.1:1, about 1.2:1, about 1.3:1, about 1.4:1, about 1.5:1, about 1.6:1, about 1.7:1, about 1.8:1, about 1.9:1, about 2:1, about 1:1.1, about 1:1.2, about 1:1.3, about 1:1.4, about 1:1.5, about 1:1.6, about 1:1.7, about 1:1.8, about 1:1.9, or about 1:2. In some embodiments, crystalline Form B has ratio of psilocybin to psilocin of about 1.3:1. In some embodiments, crystalline Form B has ratio of psilocybin to psilocin of about 1:1.

In some embodiments, crystalline Form B has a chemical purity of about 95% or greater, is about 96% or greater, is about 97% or greater, is about 98% or greater, is about 98.5% or greater, is about 99% or greater, is about 99.5% or greater, or is about 99.8% or greater. In some embodiments, crystalline Form B is substantially pure.

In some embodiments, crystalline Form B contains not more than about 0.01 mol %, about 0.02 mol %, about 0.03 mol %, about 0.04 mol %, about 0.05 mol %, about 0.06 mol %, about 0.07 mol %, about 0.08 mol %, about 0.09 mol %, about 0.1 mol %, about 0.15 mol %, about 0.2 mol %, about 0.25 mol %, about 0.3 mol %, about 0.35 mol %, about 0.4 mol %, about 0.45 mol %, about 0.5 mol %, about 0.55 mol %, about 0.6 mol %, about 0.65 mol %, about 0.7 mol %, about 0.75 mol %, about 0.8 mol %, about 0.85 mol %, about 0.9 mol %, about 0.95 mol %, about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, about 20 mol %, of other solid forms, e.g., amorphous form. In some embodiments, crystalline Form B of is substantially free of other solid forms.

In some embodiments, crystalline Form B is anhydrous.

In some embodiments, crystalline Form B is a salt formed between psilocin and psilocybin.

In some embodiments, crystalline Form B is a co-crystal formed between psilocin and psilocybin.

In some embodiments, the crystalline form of the composition comprising psilocin and psilocybin is crystalline Form C.

In some embodiments, crystalline Form C is characterized by a XRPD pattern comprising a significant peak at a 2θ angle of about 9.18°. In some embodiments, crystalline Form C is characterized by a XRPD pattern of crystalline Form C may additionally comprise a significant peak at 2θ angle of about 17.95°. In some embodiments, crystalline Form C is characterized by a XRPD pattern of crystalline Form C may additionally comprise significant peaks at 2θ angles of about 10.42°, about 24.22°, and about 18.38°. In some embodiments, crystalline Form C is characterized by a XRPD pattern of crystalline Form C may additionally comprise significant peaks at 2θ angles of about 19.82°, about 17.46°, about 14.82°, about 22.38°, and about 14.06°. In some embodiments, crystalline Form C is characterized by an XRPD pattern of FIG. 3.

Figure 8:
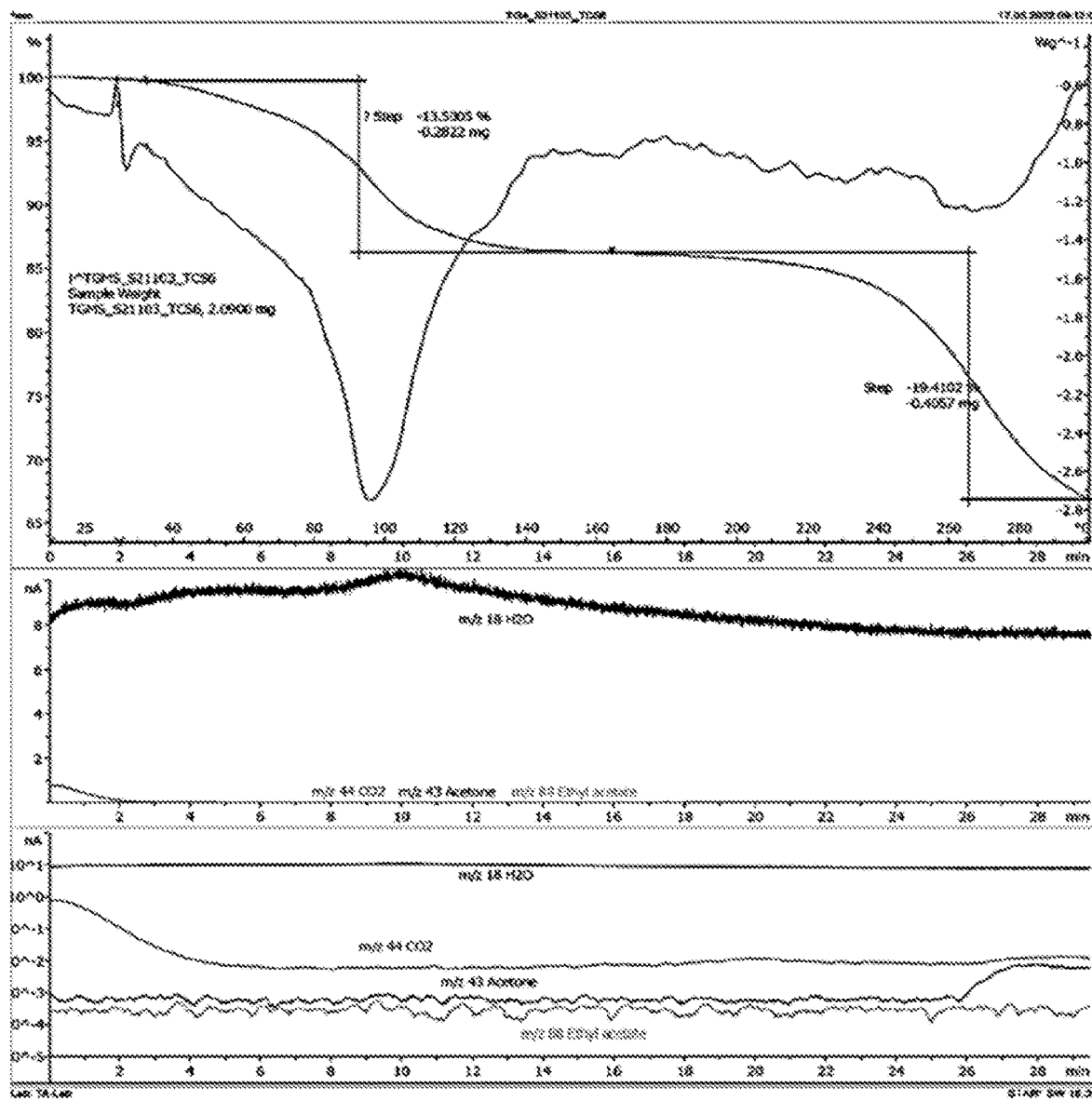
FIG. 8 shows TGMS thermogram plot of crystalline Form C.

In one embodiment, crystalline Form C has a TGMS thermograph corresponding substantially to the representative TGMS thermogram as depicted in FIG. 8. In some embodiments, negligible weight loss is observed. Weight loss (13.5%) is observed between 40-160° C. by TGMS for crystalline Form C.

Figure 9:
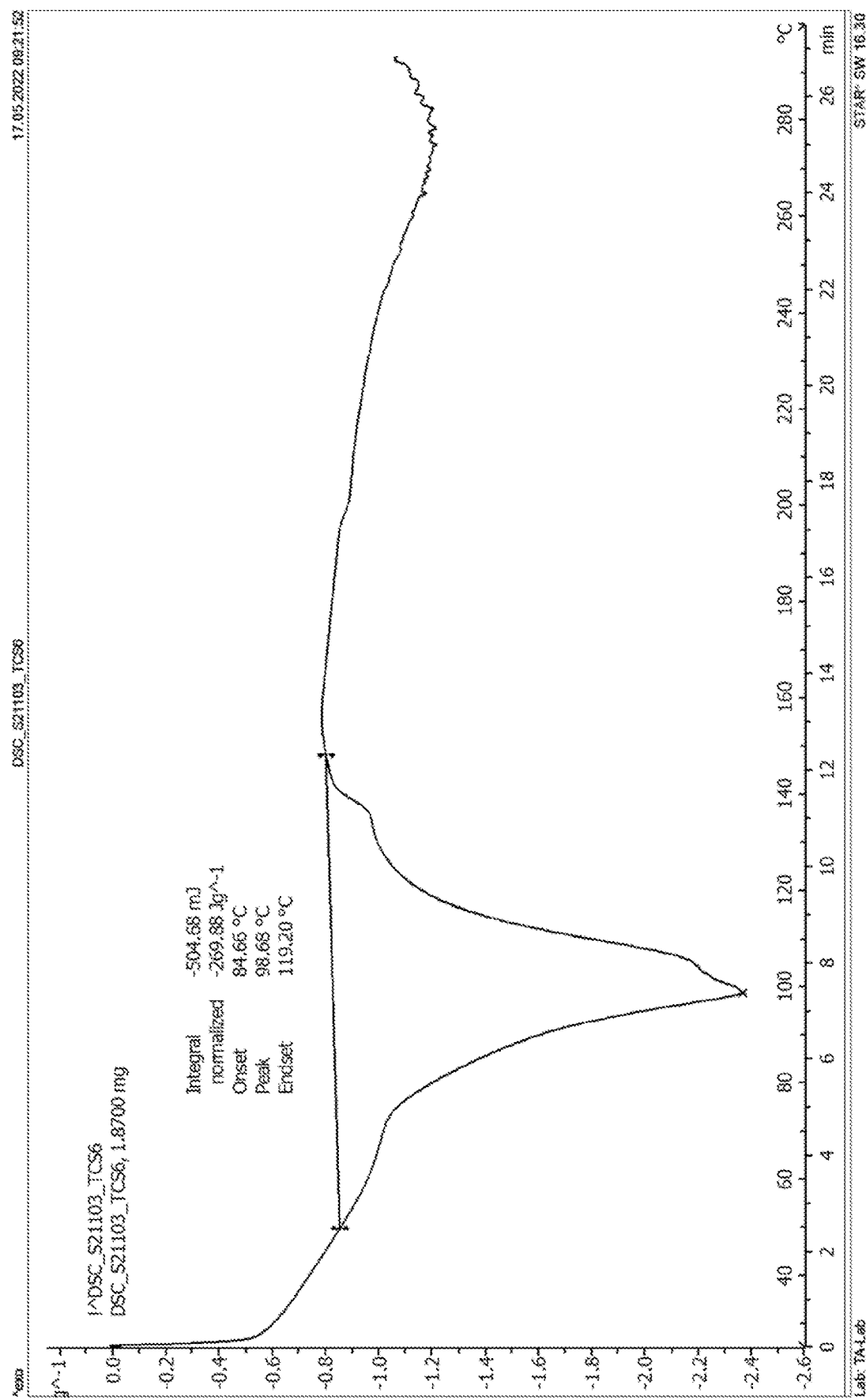
FIG. 9 shows the DSC thermogram plot of crystalline Form C.

In one embodiment, crystalline Form C has a DSC thermogram corresponding substantially as depicted in FIG. 9. In certain embodiments, crystalline Form C is characterized by a DSC plot comprising a broad endothermic event at a temperature of about 25-140° C., with a peak at 98.7° C.

In some embodiments, crystalline Form C has ratio of psilocybin to psilocin of about 1:1, about 1.1:1, about 1.2:1, about 1.3:1, about 1.4:1, about 1.5:1, about 1.6:1, about 1.7:1, about 1.8:1, about 1.9:1, about 2:1, about 1:1.1, about 1:1.2, about 1:1.3, about 1:1.4, about 1:1.5, about 1:1.6, about 1:1.7, about 1:1.8, about 1:1.9, or about 1:2. In some embodiments, crystalline Form C has ratio of psilocybin to psilocin of about 1:1.

In some embodiments, crystalline Form C has a chemical purity of about 95% or greater, is about 96% or greater, is about 97% or greater, is about 98% or greater, is about 98.5% or greater, is about 99% or greater, is about 99.5% or greater, or is about 99.8% or greater. In some embodiments, crystalline Form C is substantially pure.

In some embodiments, crystalline Form C contains not more than about 0.01 mol %, about 0.02 mol %, about 0.03 mol %, about 0.04 mol %, about 0.05 mol %, about 0.06 mol %, about 0.07 mol %, about 0.08 mol %, about 0.09 mol %, about 0.1 mol %, about 0.15 mol %, about 0.2 mol %, about 0.25 mol %, about 0.3 mol %, about 0.35 mol %, about 0.4 mol %, about 0.45 mol %, about 0.5 mol %, about 0.55 mol %, about 0.6 mol %, about 0.65 mol %, about 0.7 mol %, about 0.75 mol %, about 0.8 mol %, about 0.85 mol %, about 0.9 mol %, about 0.95 mol %, about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, about 20 mol %, of other solid forms, e.g., amorphous form. In some embodiments, crystalline Form C of is substantially free of other solid forms.

In some embodiments, crystalline Form C is anhydrous.

In some embodiments, crystalline Form C is a salt formed between psilocin and psilocybin.

In some embodiments, crystalline Form C is a co-crystal formed between psilocin and psilocybin.

Pharmaceutical Compositions

In one embodiment, the present application provides pharmaceutical composition comprising a crystalline form of psilocin and psilocybin and a pharmaceutically acceptable excipient.

In one embodiment the crystalline form is crystalline Form A, crystalline Form B or From C. In one embodiment, crystalline Form A is characterized by a XRPD pattern comprising a significant peak at a 2θ angle of about 10.1°; the XRPD pattern further comprises a significant peak at a 2θ angle of about 19.16°; at a 2θ angles of about 10.74°, about 25.3°, and about 24.07°; and/or the XRPD pattern further comprises a significant peak at a 2θ angles of about 14.54°, about 16.5°, about 13.44°, about 23.42°, and about 8.62°. In one embodiment, crystalline Form A has a ratio of psilocybin to psilocin of about 1:1. In one embodiment, crystalline Form A has a chemical purity of about 95% or greater. In some embodiments, the pharmaceutical composition of crystalline Form A contains not more than about 5 mol % of other solid forms. In some embodiments, the pharmaceutical composition of crystalline Form A of psilocin and psilocybin comprises about 95 mol % crystalline Form A, about 2.5 mol % psilocin, and about 2.5 mol % psilocybin. In one embodiment, crystalline Form A is a co-crystal formed between psilocin and psilocybin. In one embodiment, crystalline Form A is a salt formed between psilocin and psilocybin.

In one embodiment, crystalline Form A is characterized by unit cell parameters which are substantially equal to the following:

Unit cell dimensions:
 a=9.3674(3) Å
 b=11.2660(6) Å
 c=24.2741(9) Å
 α=90 degrees
 β=90 degrees
 γ=90 degrees
 Space group=P2$_1$2$_1$2$_1$
 Molecules/asymmetric unit=1

In one embodiment, L

Unit cell dimensions:
 α=9.3674(3) Å
 b=11.2660(6) Å
 c=24.2741(9) Å
 α=90 degrees
 β=90 degrees
 γ=90 degrees
 Space group=P2$_1$2$_1$2$_1$
 Molecules/asymmetric unit=1

In one embodiment, the unit cell parameters were measured about 296K. In one embodiment, crystalline Form A has a geometry of hydrogen bonds substantially as listed in Table A. In one embodiment, crystalline Form A has atomic coordinates of non-hydrogen atoms substantially as listed in Table B. In one embodiment, crystalline Form A has atomic coordinates of hydrogen atoms substantially as listed in Table C. In one embodiment, crystalline Form A is a co-crystal formed between psilocin and psilocybin. In one embodiment, crystalline Form A is a salt formed between psilocin and psilocybin.

In one embodiment, crystalline Form B is characterized by a XRPD pattern comprising a significant peak at a 2θ angle of about 18.54°; the XRPD pattern further comprises a significant peak at a 2θ angle of about 8.54°; the XRPD pattern further comprises a significant peak at a 2θ angles of about 22.78°, about 14.27°, and about 21.120 and/or the XRPD pattern further comprises a significant peak at a 2θ angles of about 14.12°, about 10.05°, about 9.94°, about 24.94°, and about 25.02°. In one embodiment, crystalline Form B has ratio of psilocybin to psilocin of about 1.3:1. In one embodiment, crystalline Form B has ratio of psilocybin to psilocin of about 1:1. In one embodiment, crystalline Form B has a chemical purity of about 95% or greater. In some embodiments, crystalline Form B contains not more than about 5 mol % of other solid forms. In some embodiments, the composition of crystalline Form B of psilocin and psilocybin comprises about 92 mol % crystalline Form B, about 2.5 mol % psilocin, and about 2.5 mol % psilocybin. In one embodiment, crystalline Form B is a co-crystal formed between psilocin and psilocybin. In one embodiment, crystalline Form B is a salt formed between psilocin and psilocybin.

In one embodiment, crystalline Form C is characterized by a XRPD pattern comprising a significant peak at a 2θ angle of about 9.18°; the XRPD pattern further comprises a significant peak at a 2θ angle of about 17.95°; the XRPD pattern further comprises a significant peak at a 2θ angles of about 10.42°, about 24.22°, and about 18.38°; and/or the XRPD pattern further comprises a significant peak at a 2θ angles of about 19.820, about 17.46°, about 14.82°, about 22.38°, and about 14.06°. In one embodiment, crystalline Form C has ratio of psilocybin to psilocin of about 1:1. In one embodiment, crystalline Form C has a chemical purity of about 95% or greater. In some embodiments, crystalline Form C contains not more than about 5 mol % of other solid forms. In some embodiments, the composition of crystalline Form C of psilocin and psilocybin comprises about 95 mol % crystalline Form C, about 2.5 mol % psilocin, and about 2.5 mol % psilocybin. In one embodiment, crystalline Form C is a co-crystal formed between psilocin and psilocybin. In one embodiment, crystalline Form C is a salt formed between psilocin and psilocybin.

The terms "treat," "treated," "treating", or "treatment" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total, whether induction of or maintenance of), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease and prolonging disease-free survival as compared to disease-free survival if not receiving treatment and prolonging disease-free survival as compared to disease-free survival if not receiving treatment.

The term "treatment" is used interchangeably herein with the term "therapeutic method" and refers to both 1) therapeutic treatments or measures that cure, slow down, lessen symptoms of, and/or halt progression of a diagnosed pathologic conditions or disorder, and 2) and prophylactic/preventative measures. Those in need of treatment may include individuals already having a particular medical disorder as well as those who may ultimately acquire the disorder (i.e., those needing preventive measures).

The terms "therapeutically effective amount", "effective dose," "therapeutically effective dose", "effective amount," or the like refer to that amount of the subject compound that will elicit the biological or medical response of a tissue, system, animal or human that is being sought by the researcher, veterinarian, medical doctor or other clinician. Generally, the response is either amelioration of symptoms in a patient or a desired biological outcome (e.g., amelioration of symptoms of PTSD). The effective amount can be determined as described herein.

The terms "administration of" and or "administering" should be understood to mean providing a pharmaceutical composition in a therapeutically effective amount to the subject in need of treatment. Administration routes can be enteral, topical or parenteral. As such, administration routes include but are not limited to intracutaneous, subcutaneous, intravenous, intraarterial, intraorbital, intracardiac, intradermal, transdermal, subarachnoid, intraspinal, oral, sublingual buccal, rectal, nasal administrations, as well infusion. Suitable unit dosage forms, include, but are not limited to powders, tablets, pills, capsules, lozenges, suppositories, patches, nasal sprays, injectables, implantable sustained-release formulations, lipid complexes, etc.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

Mental health disorders, or mental illness, refer to a wide range of disorders that include, but are not limited to, mood disorders, depressive disorders, mood instability disorders, mixed anxiety and depressive disorder, bipolar disorders, anxiety disorders, generalized anxiety disorders, social anxiety disorders, phobic disorders, panic attack disorders, schizophrenia, psychosis, schizoaffective disorders, eating disorders, anorexia nervosa, bulimia nervosa, substance misuse disorders, addiction disorders, alcohol abuse or dependence, opiate abuse or dependence, cocaine abuse or dependence, mixed drug abuse or dependence, behavioral addictions, gambling disorder, trauma-related disorders, post-traumatic stress disorders, grief-related disorders, loss-related disorders, end-of-life related disorders, cancer disorders, attention deficit disorder (ADD), attention deficit and hyperactivity disorder (ADHD), personality disorders, and obsessive compulsive disorders, and any combinations of these. The full list of currently accepted mental health disorders is given in the Diagnostic and Statical Manual, 5th edition (DSM5) which is incorporated by reference herein in its entirety. The central nervous system (CNS) disorders include, but are not limited to, both psychological and physical trauma following burns, injury, or any other physical cause, post-amputation, post brain-injury, post-stroke, post heart attack, post-diabetes, chronic pain disorders, migraines, chronic headaches, chronic back pain, chronic arthritic pain, chronic pain from any cause, cognitive disorders, cognitive deterioration, Alzheimer's Disorder, dementia at any stage, dementia from any cause, age-associated memory impairment, neuropsychiatric disorders, fetal alcohol spectrum (FAS) disorders, autism spectrum disorders, multiple sclerosis, Parkinson's disease, Fragile X, Down's syndrome, fatigue, chronic fatigue, insomnia from any cause, and all post-covid syndromes. The severity of symptoms varies such that some individuals experience debilitating disease that precludes normal social function, while others suffer with intermittent repeated episodes across their lifespan. Although the presentation and diagnostic criteria among mental illness and CNS conditions are distinct in part, there are common endophenotypes of note across the diseases, and often comorbidities exist.

Specifically, there exist phenotypic endophenotypes associated with alterations in mood, cognition and behavior. Interestingly, many of these endophenotypes extend to neurological conditions as well. For example, attentional deficits are reported in patients with attention deficit disorder, attention deficit hyperactivity disorder, eating disorders, substance use disorders, schizophrenia, depression, obsessive compulsive disorder, traumatic brain injury, Fragile X, Alzheimer's disease, Parkinson's disease and frontotemporal dementia.

Depressive disorders are characterized by low mood, feeling sad or hopeless, increased irritability, sleep disturbance, lowered energy and feeling tired, poor concentration, lowered self-esteem or feeling worthless, lack of interest or pleasure in things, slowed movement, thinking they would be better off dead and self-harm, and actively considering and attempting suicide, and include major depressive disorder, bipolar depression, treatment resistant depression, and dysthymic disorder.

Anxiety disorders are characterized by feeling nervous, anxious, having difficulty breathing, avoiding people or activities, worrying excessively, physical symptoms including chest pain, palpitations of the heart, sweating, nausea, stomach ache, headache, neckache, poor sleep, poor concentration, sweating, and dizziness and include generalized anxiety disorder, social anxiety disorder, panic disorder, agoraphobia, phobias, and separation anxiety disorder.

Post-traumatic stress disorder is characterized by flashbacks, nightmares, involuntary memories, emotional distress or physical reactions after being reminded of the trauma, avoidance of anything that can trigger such remembrances, avoiding activities, social isolation, increased anger or aggression, increased irritability, participating in risky behavior, poor concentration, problems sleeping, and an increased startle response, which can further be described as those with dissociated experiences.

Substance abuse and Addiction disorders are identified when and individual has recurrent use of alcohol or drugs which cause significant impairment in issues negatively impacting health, work, school, and home, with the severity depending upon the type and frequency of substance use, social and interpersonal problems related to this use, impact on family, friends, work, school, and relationships, withdrawal symptoms, tolerance, unsuccessful attempts to stop, physical and mental health problems from this use, and cravings, and include alcohol use disorder, cannabis use disorder, hallucinogen use disorder, inhalant use disorder, opioid use disorder, sedative hypnotic or anxiolytic use disorder, stimulant use disorder, tobacco use disorder, unknown substance use disorder, with these disorders occurring either alone or in combination.

Chronic pain disorders are characterized by pain in one or more regions of the body including headache, low back pain, neck pain, arthritis pain, pain in context of cancer, neurogenic pain, psychogenic pain, and include conditions such as chronic arthritis, osteoarthritis, chronic fatigue syndrome, endometriosis, fibromyalgia, inflammatory bowel disease, interstitial cystitis, temporomandibular joint dysfunction, vulvodynia, cluster headaches, migraine, herpes zoster, frozen shoulder, complex regional pain syndrome, gout, post-surgical pain syndrome, prolapsed intervertebral disc, sciatica, and trigeminal neuralgia.

Cognitive disorders are characterized by poor functioning of the brain such that memory and other functions deteriorate including movement, speech, concentration and focus, problem-solving, analyzing sleep, tremors, tiredness, dizziness, headaches, hallucinations and confabulation, and include age-associated memory impairment, Alzheimer's disease, Picks disease, vascular dementia, post-stroke dementia, multi-infarct dementia, Parkinson's disease, frontal-lobe dementia, alcohol-induced dementia, and amnesia disorders including Korsakoff's syndrome.

In one embodiment, there is provided a crystalline form of psilocybin and psilocin, crystalline Form A, crystalline Form B, crystalline Form C or combinations thereof, for use in treating post-traumatic stress disorder (PTSD). In one embodiment, there is provided a crystalline form of psilocybin and psilocin, crystalline Form A, crystalline Form B, crystalline Form C or combinations thereof, for use in treating treatment resistant PTSD. In one embodiment, there is provided a crystalline form of psilocybin and psilocin, crystalline Form A for use in treating treatment resistant PTSD. In one embodiment, there is provided a crystalline form of psilocybin and psilocin crystalline Form B for use in treating treatment resistant PTSD. In one embodiment, there is provided a crystalline form of psilocybin and psilocin crystalline Form C for use in treating treatment resistant PTSD. In one embodiment, there is provided a high purity crystalline form of psilocybin and psilocin crystalline Form A for use in treating treatment resistant PTSD. In one embodiment, there is provided a high purity crystalline form of psilocybin and psilocin crystalline Form B for use in treating treatment resistant PTSD. In one embodiment, there is provided a high purity crystalline form of psilocybin and psilocin crystalline Form C for use in treating treatment resistant PTSD.

In one embodiment, there is provided a method of treating PTSD comprising administering to a subject in need thereof an effective dose of a crystalline form of psilocybin and psilocin, crystalline Form A, crystalline Form B, crystalline Form C or combinations thereof. In one embodiment, there is provided a method of treating treatment resistant PTSD comprising administering to a subject in need thereof an effective dose of a crystalline form of psilocybin and psilocin, crystalline Form A, crystalline Form B, crystalline Form C or combinations thereof. In one embodiment, there is provided a method of treating treatment resistant PTSD comprising administering to a subject in need thereof an effective dose of a crystalline form of psilocybin and psilocin crystalline Form A. In one embodiment, there is provided a method of treating treatment resistant PTSD comprising administering to a subject in need thereof an effective dose of a crystalline form of psilocybin and psilocin crystalline Form B. In one embodiment, there is provided a method of treating treatment resistant PTSD comprising administering to a subject in need thereof an effective dose of a crystalline form of psilocybin and psilocin crystalline Form C.

In one embodiment, there is provided a crystalline form of psilocybin and psilocin, crystalline Form A, crystalline Form B, crystalline Form C or combinations thereof, for use in treating depression. In one embodiment, there is provided a crystalline form of psilocybin and psilocin, crystalline Form A, crystalline Form B, crystalline Form C or combinations thereof, for use in treating drug resistant depression.

In one embodiment, there is provided a crystalline form of psilocybin and psilocin, crystalline Form A for use in treating drug resistant depression. In one embodiment, there is provided a crystalline form of psilocybin and psilocin crystalline Form B for use in treating drug resistant depression. In one embodiment, there is provided a crystalline form of psilocybin and psilocin crystalline Form C for use in treating drug resistant depression. In one embodiment, there is provided a high purity crystalline form of psilocybin and psilocin crystalline Form A for use in treating drug resistant depression. In one embodiment, there is provided a high purity crystalline form of psilocybin and psilocin crystalline Form B for use in treating drug resistant depression. In one embodiment, there is provided a high purity crystalline form of psilocybin and psilocin crystalline Form C for use in treating drug resistant depression.

In one embodiment, there is provided a method of treating depression comprising administering to a subject in need thereof an effective dose of a crystalline form of psilocybin and psilocin, crystalline Form A, crystalline Form B, crystalline Form C or combinations thereof. In one embodiment, there is provided a method of treating drug resistant depression comprising administering to a subject in need thereof an effective dose of a crystalline form of psilocybin and psilocin, crystalline Form A, crystalline Form B, crystalline Form C or combinations thereof. In one embodiment, there is provided a method of treating drug resistant depression comprising administering to a subject in need thereof an effective dose of a crystalline form of psilocybin and psilocin crystalline Form A. In one embodiment, there is provided a method of treating drug resistant depression comprising administering to a subject in need thereof an effective dose of a crystalline form of psilocybin and psilocin crystalline Form B. In one embodiment, there is provided a method of treating drug resistant depression comprising administering to a subject in need thereof an effective dose of a crystalline form of psilocybin and psilocin crystalline Form C.

The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLES

Example 1

Salt Screen

Lyophilization/recrystallization: Physical mixtures of psilocin and psilocybin in a 1:1 ratio were be prepared in Water:Acetonitrile (60:40 v/v)+0.1% formic acid. The solution was split over 11 vials to achieve 30 mg of psilocin content in each vial. The solvent was removed by freeze-drying. The obtained amorphous material was then resuspended in 10 solvents and the samples were heated to 50° C. and cooled to 5° C. with a constant heating rate of 10° C./h and variable cooling rates of −20° C./h, −10° C./h and −5° C./h from the first to the third cycle. After the temperature profile, the solids were harvested ambient and vacuum dried and analyzed by XPRD. All the solids were then exposed to 2 days at 40° C./75% RH (AAC) and remeasured by XRPD. Results are shown in Table 1.

TABLE 1

| | | | HT-XRPD | | | |
|---|---|---|---|---|---|---|
| Exp ID | Solvent | Concentration (mg/mL) | Ambient-dried | Vacuum-dried | AAC-Amb-dried | AAC-Vacuum-dried |
| TCS1 | 1,4-dioxane | 157.5 | Amorphous | crystalline Form A pc | crystalline Form C pc | crystalline Form C pc |
| TCS2 | Ethanol | 163.7 | crystalline Form A | crystalline Form A | crystalline Form A | crystalline Form A |
| TCS3 | Acetone | 92.1 | crystalline Form A pc | crystalline Form A pc | crystalline Form C pc | crystalline Form C pc |
| TCS4 | Acetonitrile | 90.0 | Amorphous | Amorphous | crystalline Form C | crystalline Form C pc |
| TCS5 | MEK | 214.1 | crystalline Form A pc | crystalline Form A pc | crystalline Form C | crystalline Form C pc |
| TCS6 | EtOAc | 204.7 | Amorphous | Amorphous | crystalline Form C pc | crystalline Form C pc |
| TCS7 | TBME | 123.8 | | Amorphous | crystalline Form C | crystalline Form C pc |
| TCS8 | 2-propanol | 117.4 | Amorphous | | crystalline Form C pc | crystalline Form C |
| TCS9 | THF | 133.7 | Amorphous | crystalline Form A pc | crystalline Form C | crystalline Form C |
| TCS10 | n-heptane | 79.3 | Amorphous | crystalline Form A pc | crystalline Form C pc | crystalline Form C pc | pc = poor crystalline

Slurry Conversion: Physical mixtures of Psilocin and Psilocybin in a molar ratio were prepared in organic solvent mixtures to form suspensions. Samples were heated to 50° C. and cooled to 5° C. with a constant heating rate of 10° C./h and variable cooling rates of −20° C./h, −10° C./h and −5° C./h from the first to the third cycle. Afterwards, the samples were aged at RT for 72 hours. Upon completion of the aging time, the solids were separated from the liquid phases by centrifugation and dried under ambient conditions and under vacuum before being analyzed by HT-XRPD. All solids were exposed to 2 days at 40° C./75% RH (AAC) and remeasured by XRPD. Results are shown in Table 2.

TABLE 2

| Exp ID | Psilocin (mg) | Psilocybin (mg) | Solvent | Volume (mL) | Solids after Temperature profile? | HT-XRPD Ambient-dried | HT-XRPD Vacuum-dried | HT-XRPD AAC-Amb-dried | HT-XRPD AAC-Vacuum-dried |
|---|---|---|---|---|---|---|---|---|---|
| TCS22 | 14.59 | 24.33 | TFE/IPA 10/90 | 250 | Yes | crystalline Form A | crystalline Form A | crystalline Form A | crystalline Form A |
| TCS23 | 14.63 | 23.74 | TFE/Isopropyl acetate 10/90 | 250 | Yes | crystalline Form A | crystalline Form A | crystalline Form A | crystalline Form A |
| TCS24 | 14.09 | 23.82 | TFE/Toluene 10/90 | 200 | Yes | crystalline Form B | crystalline Form B | crystalline Form B | crystalline Form B |
| TCS25 | 14.13 | 23.68 | Acetonitrile/water 80/20 | 250 | Yes | crystalline Form C pc | pc | crystalline Form C pc | crystalline Form C |
| TCS26 | 14.78 | 24.22 | THF/water 80/20 | 300 | Yes | crystalline Form C | pc | crystalline Form C | crystalline Form C | pc = poor crystalline

Example 2

XRPD Analysis

XRPD patterns were obtained using the Ardena T2 high-throughput XRPD set-up. The plates were mounted on a Bruker General Area Detector Diffraction System (GADDS) equipped with a VÅNTEC-500 gas area detector corrected for intensity and geometric variations. The calibration of the measurement accuracy (peaks position) was performed using NIST SRM1976 standard (Corundum).

Data collection was carried out at room temperature using monochromatic Cu Kα radiation in the 2θ region between 1.5° and 41.5°, which is the most distinctive part of the XRPD pattern. The diffraction pattern of each well was collected in two 2θ ranges (1.5°≤2θ ≤21.5° for the first frame, and 19.5°≤2θ≤41.5° for the second) with an exposure time of 90 s for each frame. No background subtraction or curve smoothing was applied to the XRPD patterns.

Cell parameters as well as crystal system were obtained using LSI-Index (Coelho, 2003; Coelho & Kern, 2005) indexing program. The space group was selected on reflections condition and density of the crystal. The cell parameters, purity as well as instrument parameters were refined using Whole Powder Pattern Decomposition method.

For Rietveld calculation the cell parameters, crystal system as well as atom positions were taken from the single crystal file (cif). During the refinement the following parameters were refined: cell constants, background, instrument geometry, zero shift, and absorption.

Nor atom positions neither thermal motion parameters were refined during whole process. The following criteria of fit were used:

Yo,m and Yc,m are the observed and calculated data, respectively at data point m, M the number of data points, P the number of parameters, wm the weighting given to data point m which for counting statistics is given by wm=1/σ (Yo,m)2 where σ(Yo,m) is the error in Yo,m, $$R_{exp} = \sqrt{\frac{M-P}{\sum w_m Y_{o,m}^2}} \ ; \ R_{wp} = \sqrt{\frac{\sum w_m(Y_{o,m}-Y_{c,m})^2}{\sum w_m Y_{o,m}^2}} \ ;$$

$$R_p = \sqrt{\frac{\sum |Y_{o,m}-Y_{c,m}|}{\sum Y_{o,m}}}$$

$$GOF = chi^2 = \frac{R_{wp}}{R_{exp}} = \sqrt{\frac{\sum w_m(Y_{o,m}-Y_{c,m})^2}{M-P}}$$

The XRPD of crystalline Form A from Exp ID TCS2 is shown in FIG. 1 with the peak table shown in Table 3.

TABLE 3

| PEAK ID | ANGLE (2Θ) | D-SPACING | INTENSITY |
|---|---|---|---|
| 1 | 8.62 | 10.24 | 26.92 |
| 2 | 10.1 | 8.75 | 74.3 |
| 3 | 10.67 | 8.28 | 41 |
| 4 | 10.74 | 8.23 | 41.53 |
| 5 | 11.91 | 7.42 | 24.79 |
| 6 | 12.78 | 6.92 | 25.41 |
| 7 | 12.86 | 6.88 | 24.14 |
| 8 | 13.44 | 6.58 | 29.73 |
| 9 | 14.47 | 6.12 | 32.64 |
| 10 | 14.54 | 6.08 | 34.64 |
| 11 | 16.5 | 5.37 | 32.75 |
| 12 | 16.57 | 5.34 | 31.21 |
| 13 | 17.38 | 5.1 | 22.03 |
| 14 | 19.16 | 4.63 | 53.76 |
| 15 | 19.78 | 4.48 | 23.48 |
| 16 | 19.86 | 4.47 | 24.04 |
| 17 | 23.42 | 3.79 | 28.95 |
| 18 | 23.58 | 3.77 | 22.25 |
| 19 | 24.07 | 3.69 | 39.17 |
| 20 | 24.18 | 3.68 | 38.57 |
| 21 | 25.22 | 3.53 | 39.39 |
| 22 | 25.3 | 3.52 | 40.24 |
| 23 | 26.46 | 3.36 | 11.13 |
| 24 | 26.58 | 3.35 | 11.27 |
| 25 | 27.51 | 3.24 | 11.77 |
| 26 | 27.62 | 3.23 | 15.04 |

Figure 2:
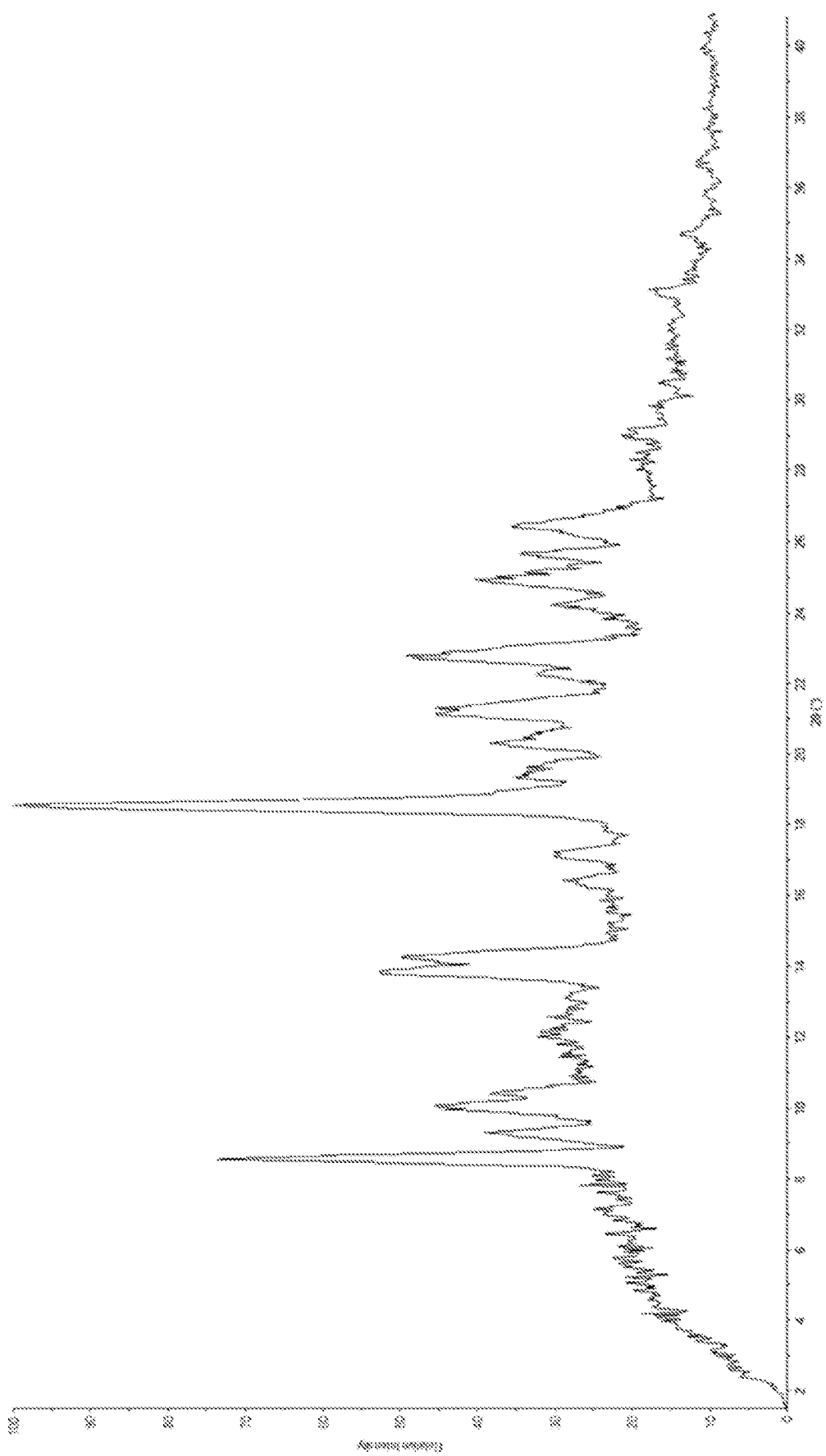
FIG. 2 shows an XRPD plot of crystalline Form B.

The XRPD of crystalline Form B from Exp ID TCS24 is shown in FIG. 2 with the peak table shown in Table 4.

TABLE 4

| PEAK ID | ANGLE (2Θ) | D-SPACING | INTENSITY |
|---|---|---|---|
| 1 | 8.54 | 10.34 | 51.89 |
| 2 | 9.3 | 9.5 | 17.17 |
| 3 | 9.94 | 8.89 | 22.07 |
| 4 | 10.05 | 8.79 | 23.38 |

TABLE 4-continued

| PEAK ID | ANGLE (2Θ) | D-SPACING | INTENSITY |
|---|---|---|---|
| 5 | 10.39 | 8.51 | 16.39 |
| 6 | 14.12 | 6.27 | 23.75 |
| 7 | 14.27 | 6.2 | 28.34 |
| 8 | 18.54 | 4.78 | 78.66 |
| 9 | 19.34 | 4.58 | 14.35 |
| 10 | 20.3 | 4.37 | 17.49 |
| 11 | 20.46 | 4.33 | 13.31 |
| 12 | 21.12 | 4.2 | 24.94 |
| 13 | 22.78 | 3.9 | 29.16 |
| 14 | 24.94 | 3.57 | 21.53 |
| 15 | 25.02 | 3.55 | 18.84 |
| 16 | 25.68 | 3.47 | 16.68 |
| 17 | 26.42 | 3.37 | 18.3 |

Figure 3:
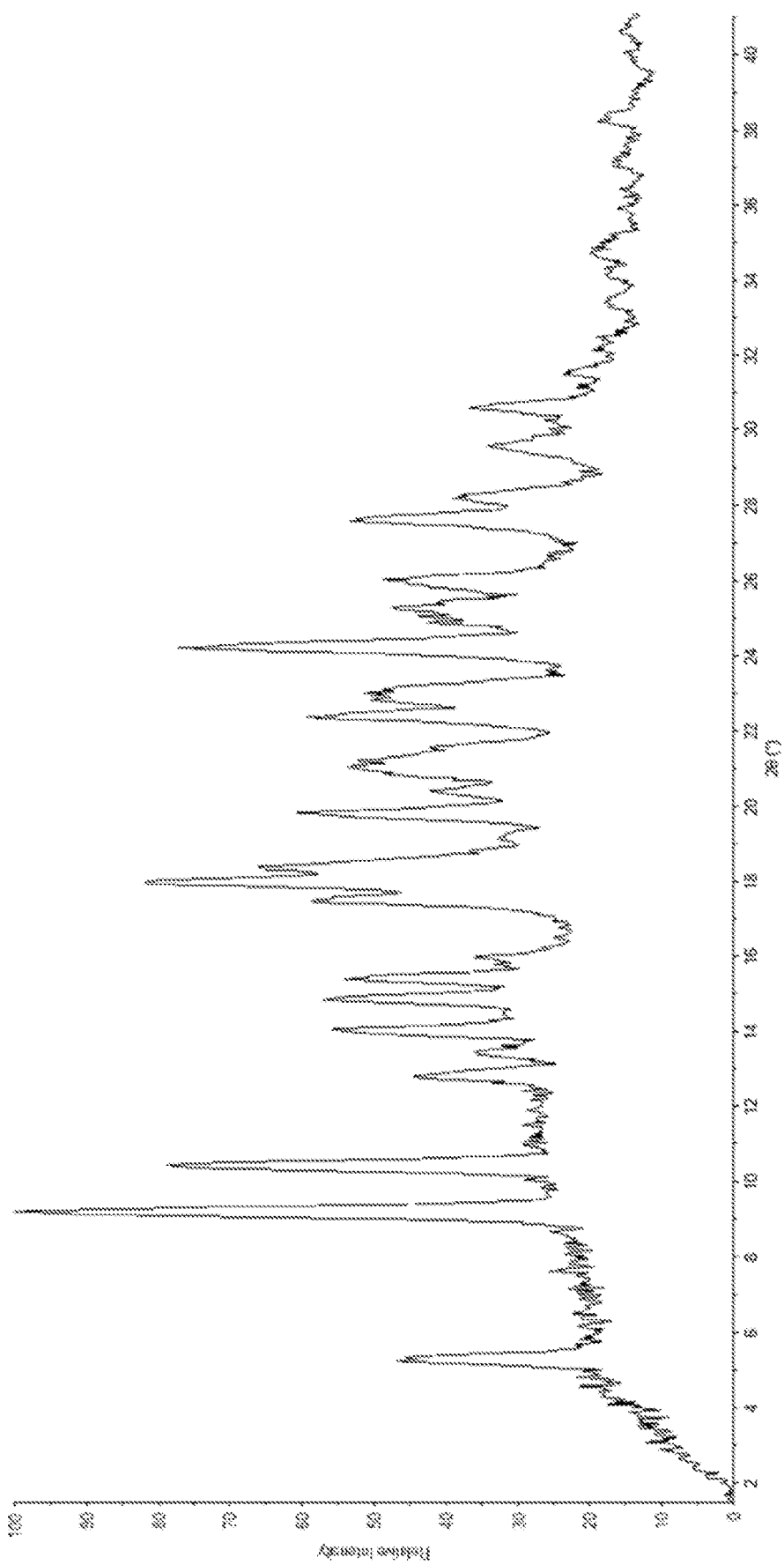
FIG. 3 shows an XRPD plot of crystalline Form C.

The XRPD of crystalline Form C from Exp ID TCS26 is shown in FIG. 3 with the peak table shown in Table 5.

TABLE 5

| PEAK ID | ANGLE (2Θ) | D-SPACING | INTENSITY |
|---|---|---|---|
| 1 | 5.26 | 16.78 | 32.39 |
| 2 | 9.18 | 9.62 | 78.06 |
| 3 | 10.42 | 8.48 | 56.63 |
| 4 | 14.06 | 6.29 | 33.31 |
| 5 | 14.82 | 5.97 | 34.45 |
| 6 | 15.38 | 5.75 | 31.18 |
| 7 | 17.46 | 5.07 | 35.33 |
| 8 | 17.95 | 4.94 | 58.28 |
| 9 | 18.38 | 4.82 | 42.18 |
| 10 | 19.82 | 4.47 | 36.34 |
| 11 | 22.38 | 3.97 | 34.22 |
| 12 | 24.22 | 3.67 | 52.57 |
| 13 | 25.3 | 3.52 | 24.13 |
| 14 | 27.58 | 3.23 | 32.32 |

Example 3

TGMS and DSC Analysis

Mass loss due to solvent or water loss from the crystals was determined by TGA/DSC. Monitoring the sample weight, during heating in a TGA/DSC 3+ STARe system (Mettler-Toledo GmbH, Switzerland), resulted in a weight vs. temperature curve and a heat flow signal. The TGA/DSC 3+ was calibrated for temperature with samples of indium and aluminum. Samples (circa 2 mg) were weighed into 100 µL aluminum crucibles and sealed. The seals were pin-holed, and the crucibles heated in the TGA from 25 to 300° C. at a heating rate of 10° C. min−1. Dry N2 gas was used for purging.

The gases coming from the TGA samples were analyzed by a mass spectrometer Omnistar GSD 350 (Pfeiffer Vacuum GmbH, Germany). The latter is a quadrupole mass spectrometer, which analyzes masses in the temperature range of 0-200 amu.

Thermal events were obtained from DSC thermograms, recorded with a heat flux DSC3+ STARe system (Mettler-Toledo GmbH, Switzerland). The DSC3+ was calibrated for temperature and enthalpy with a small piece of indium (m.p.=156.6° C.; δHf=28.45 J/g) and zinc (m.p.=419.6° C.; δHf=107.5 J/g). Samples (circa 2 mg) were sealed in standard 40 µL aluminum pans, pin-holed and heated in the DSC from 25° C. to 300° C., at a heating rate of 10° C./min. Dry N2 gas, at a flow rate of 50 mL/min was used to purge the DSC equipment during measurement.

The TGMS analysis of crystalline Form A showed a mass loss of 1.3% between 40 and 200° C., due to residual ethanol/water. Thermal decomposition started above 200° C. The DSC trace showed a single endothermic event at $T_{peak}$ of 255.0° C. ($T_{onset}$ 252.5° C.) which corresponds to the melting of crystalline Form A. The TGMS thermogram of crystalline Form A is shown in FIG. 4 and the DSC thermogram of crystalline Form A is shown in FIG. 5.

The TGMS analysis of crystalline Form B showed a mass loss of 15.8% between 40 and 200° C., due to TFE and toluene based on the MS signal. Thermal decomposition started above 200° C. The DSC trace showed a broad endothermic event at $T_{peak}$ of 168.2° C. ($T_{onset}$ 156.1° C.) which corresponds to the desolvation of crystalline Form B. The TGMS thermogram of crystalline Form B is shown in FIG. 6 and the DSC thermogram of crystalline Form B is shown in FIG. 7.

The TGMS analysis of crystalline Form C showed a mass loss of 13.5% between 40 and 160° C., due to water based on the MS signal. Thermal decomposition started above 160° C. The DSC trace showed a broad endothermic event between 25-140° C. ($T_{peak}$ 98.7° C., $T_{onset}$ 84.7° C.) which corresponds to the dehydration of crystalline Form C. The TGMS thermogram of crystalline Form B is shown in FIG. 8 and the DSC thermogram of crystalline Form B is shown in FIG. 9.

Example 4

NMR Spectroscopy $^1$H-NMR spectroscopy in $D_2O$ was used for compound integrity characterization of Psilocybin and Psilocybin-Psilocin polymorphs (crystalline Form A and crystalline Form B). The spectra were recorded at room temperature on a 500 MHz instrument (Bruker BioSpin GmbH) using standard pulse sequences. The data was processed with ACD Labs software Spectrus Processor 2016.2.2 (Advanced Chemistry Development Inc. Canada).

Figure 10:
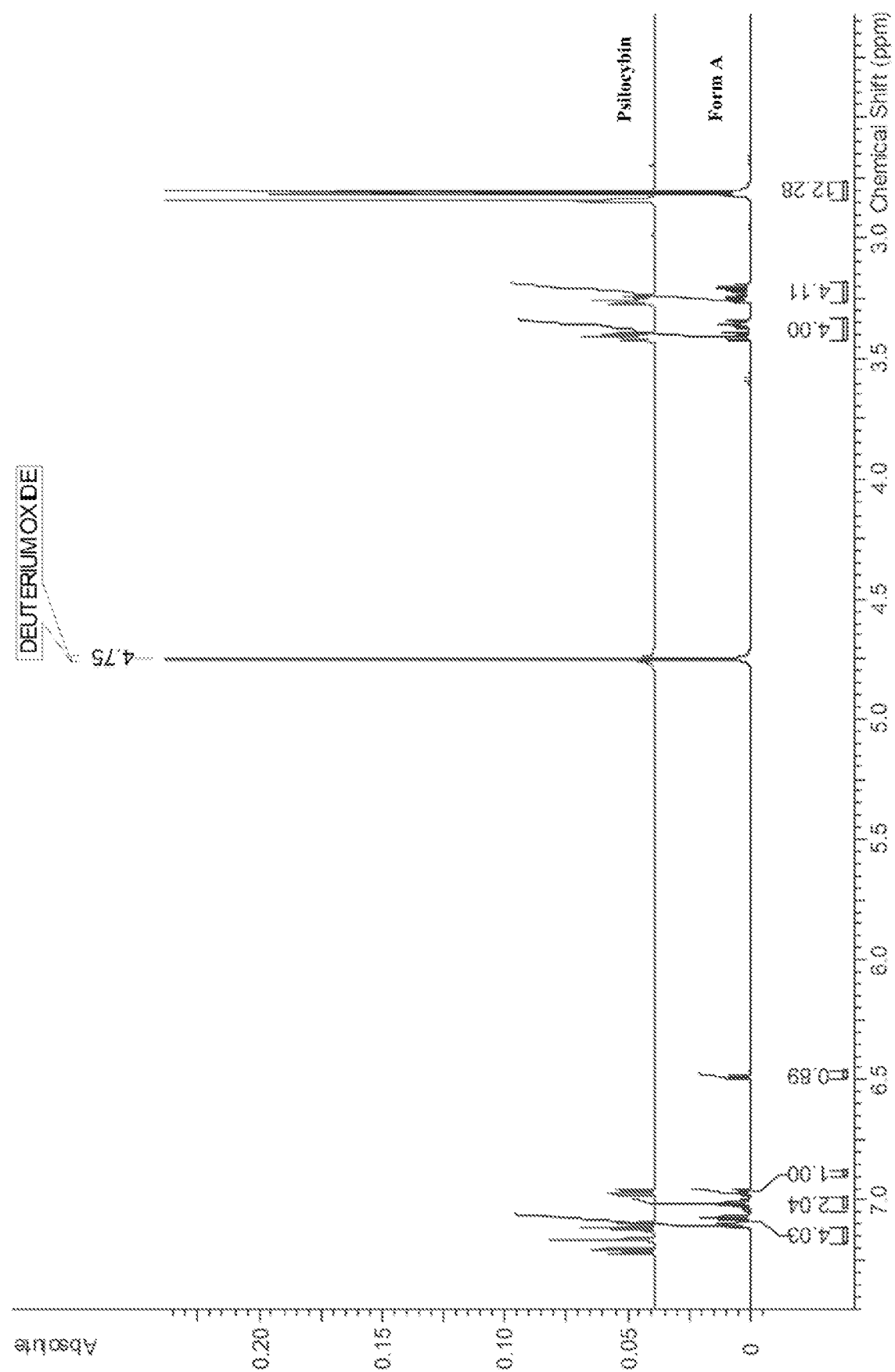
FIG. 10 shows the $^1$H-NMR of crystalline Form A and psilocybin.
Figure 11:
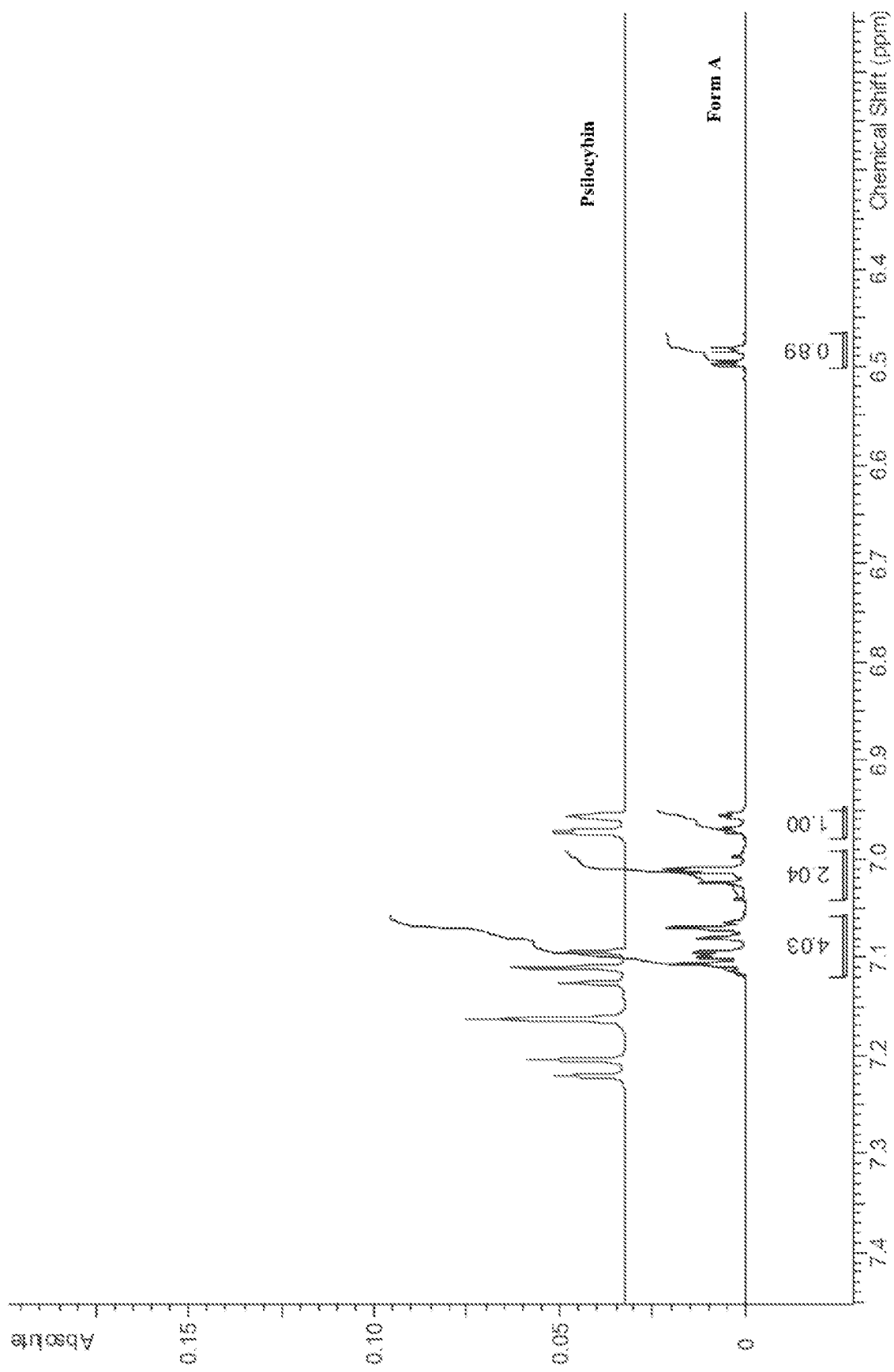
FIG. 11 shows the $^1$H-NMR of crystalline Form A and psilocybin between 6 ppm and 7.5 ppm.
Figure 12:
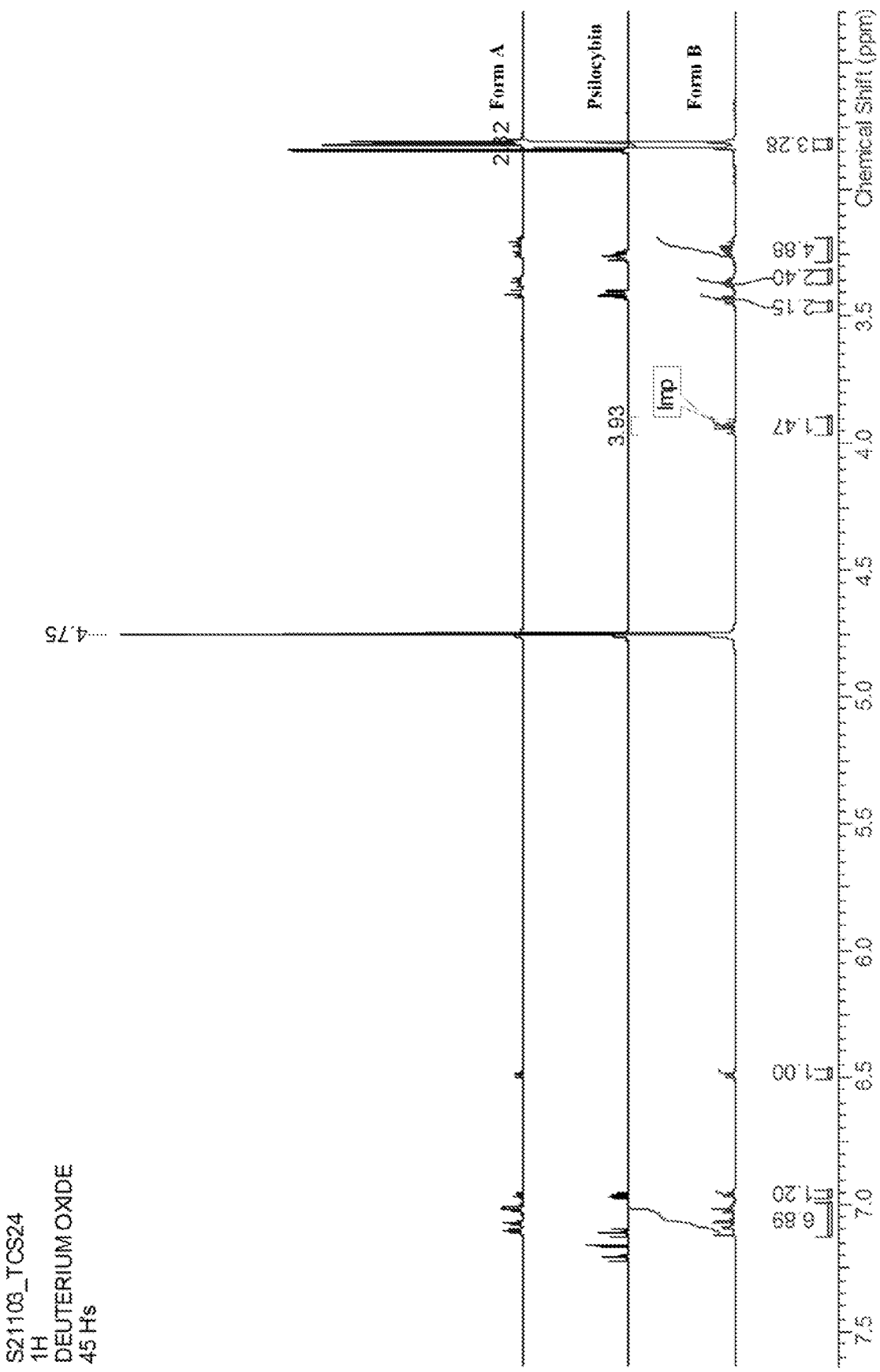
FIG. 12 shows the $^1$H-NMR of crystalline Form A, crystalline Form B, and psilocybin.
Figure 13:
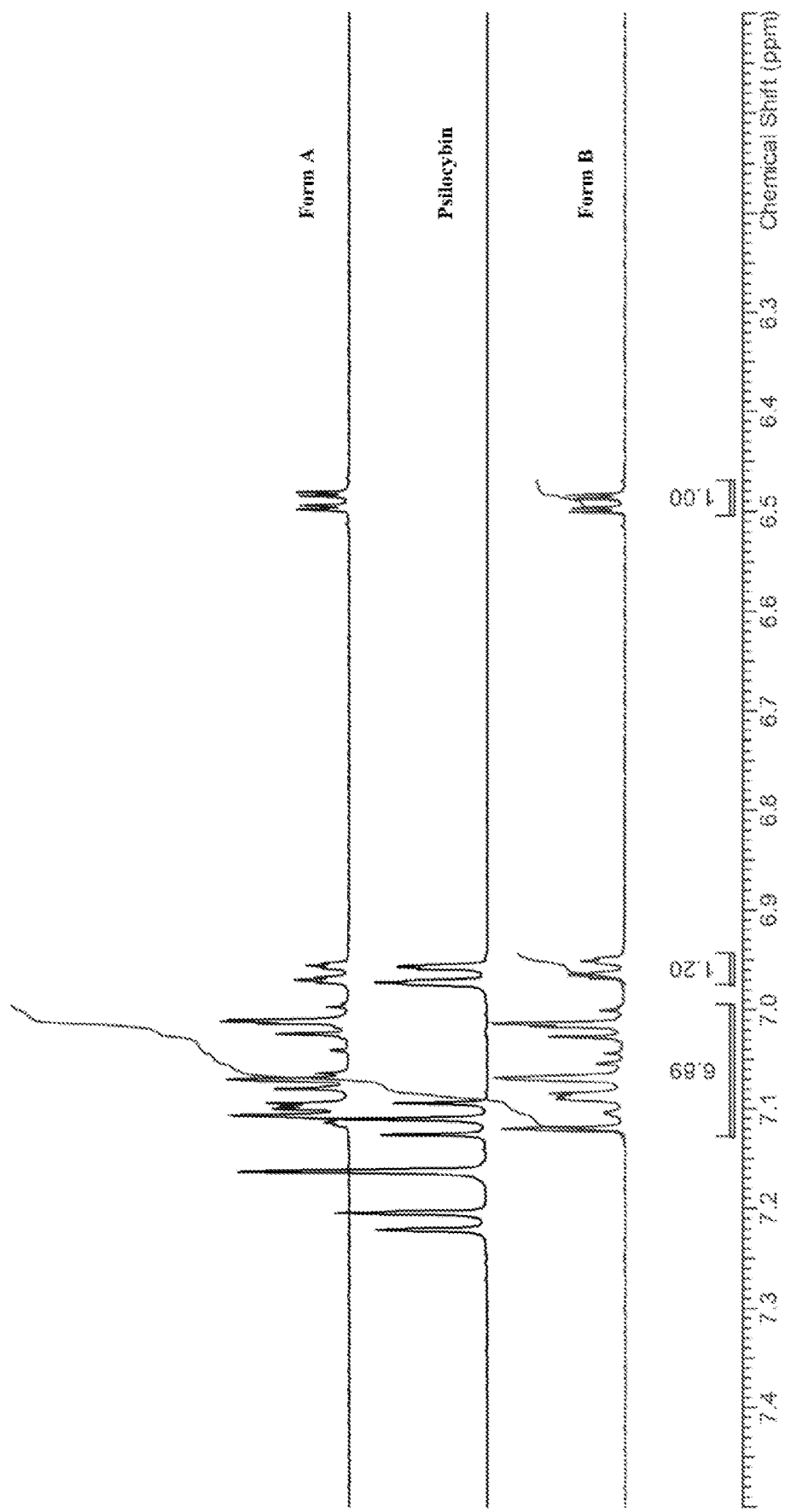
FIG. 13 shows the $^1$H-NMR of crystalline Form A, crystalline Form B, and psilocybin between 6 ppm and 7.5 ppm.

FIG. 10 overlays the $^1$H-NMR of crystalline Form A and psilocybin while FIG. 11 shows the $^1$H-NMR of crystalline Form A and psilocybin between 6 ppm and 7.5 ppm. FIG. 12 overlays the $^1$H-NMR of crystalline Form A, crystalline Form B, and psilocybin while FIG. 13 overlays the $^1$H-NMR of crystalline Form A, crystalline Form B, and psilocybin between 6 ppm and 7.5 ppm.

Example 5

DVS Analysis

Moisture sorption isotherms were collected on a DVS Adventure system from Surface Measurement Systems (London, UK). Sample size was circa 10 mg of solid material. A full sorption and desorption isotherm was recorded by varying the relative humidity from 40-95-0-40% in steps of 10% at a constant temperature of 25° C. Weight equilibration per step was set at dm/dt of 0.002%/min. Afterwards the sample was measured by HT-XRPD.

Figure 14:
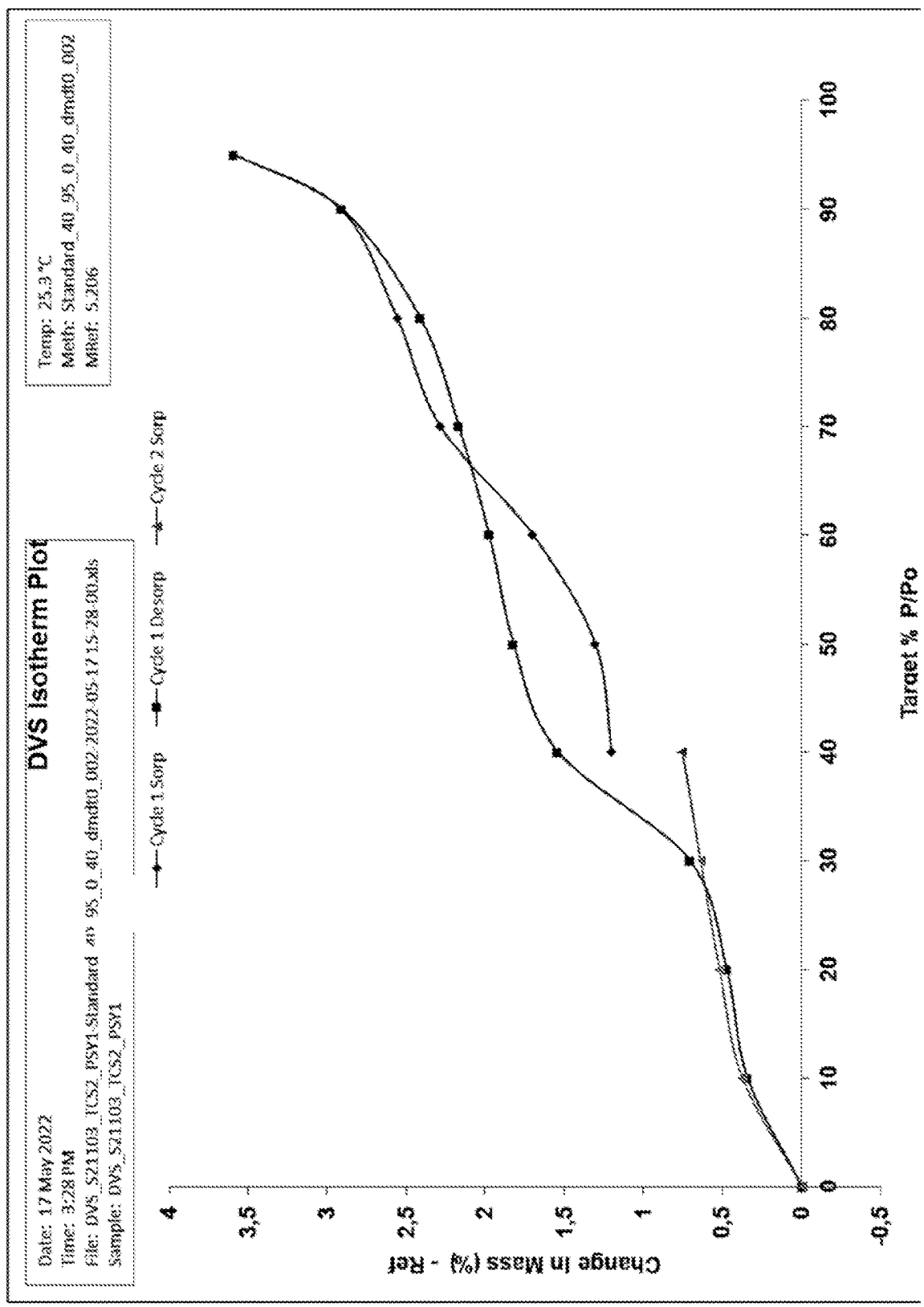
FIG. 14 shows the dynamic vapor sorption (DVS) isotherm of crystalline Form A.

Crystalline Form A: The total mass difference between 0-95% RH was 3.6%, and the mass uptake at 80% RH was 2.4%, indicating that the material is moderately hygroscopic according to the EP hygroscopicity classification. The solid recovered after DVS was analyzed by XRPD analysis which confirmed that PSY1 is physically stable after the sorption-desorption cycle. The DVS isotherm of crystalline Form A is depicted in FIG. 14.

Figure 15:
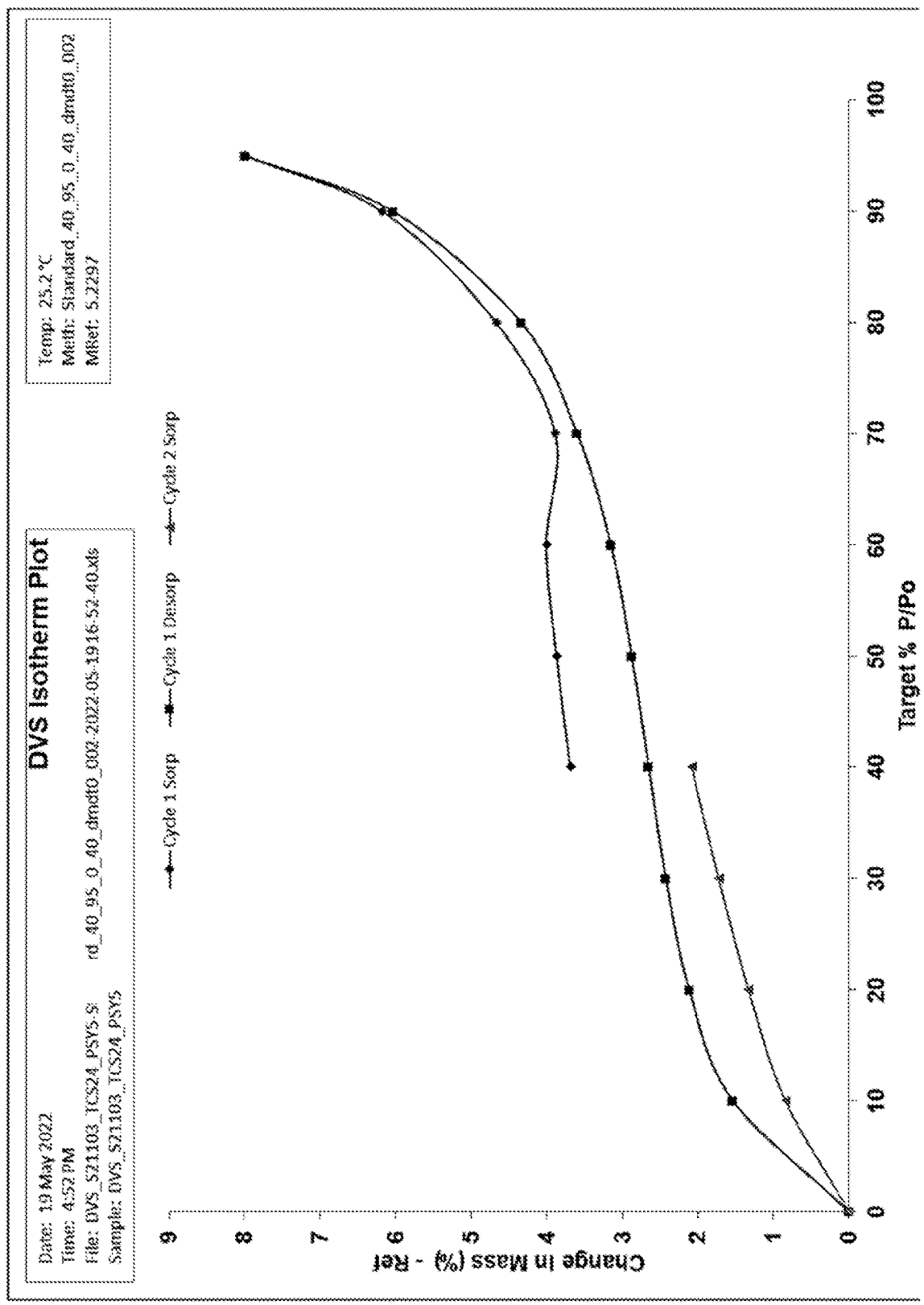
FIG. 15 shows the DVS isotherm of crystalline Form B.

Crystalline Form B: The total mass difference between 0-95% RH was 8.0%, and the mass uptake at 80% RH was 4.3%, indicating that the material is moderately hygroscopic according to the EP hygroscopicity classification. The solid recovered after DVS was analyzed by XRPD analysis which confirmed that PSY5 is physically stable after the sorption-desorption cycle. The DVS isotherm of crystalline Form B is depicted in FIG. 15.

Figure 16:
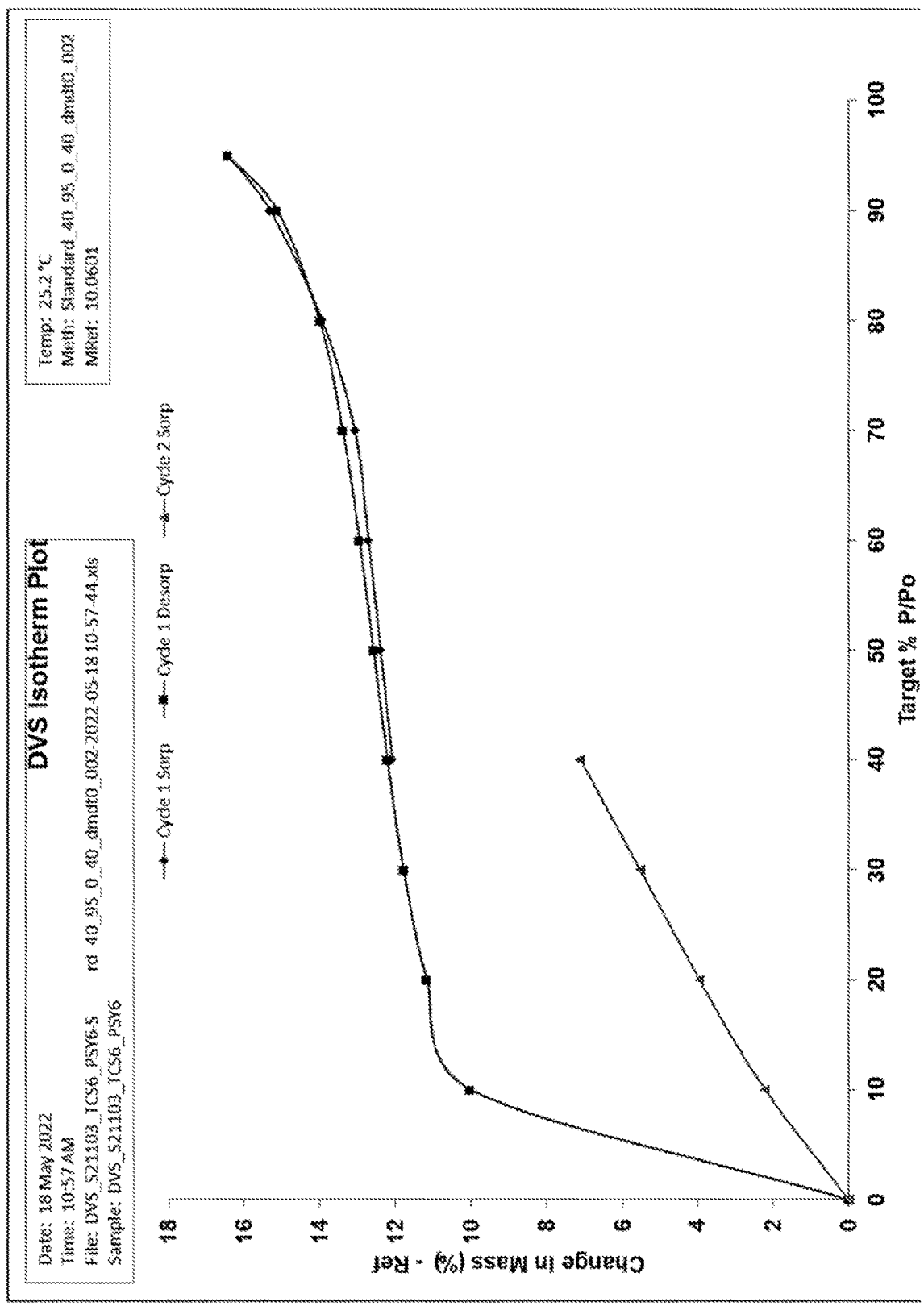
FIG. 16 shows the DVS isotherm of crystalline Form C.

Crystalline Form C: The total mass difference between 0-95% RH was 16.4%, and the mass uptake at 80% RH was 1.8%, indicating that the material is slightly hygroscopic according to the EP hygroscopicity classification. The solid recovered after DVS was analyzed by XRPD which confirmed that crystalline Form C is physically stable after sorption-desorption cycle. The gradual water uptake between 20-95% RH was 5.2% which corresponds to 1.5 molecules of water. The DVS isotherm of crystalline Form B is depicted in FIG. 16.

Example 6

UPLC Analysis

UPLC Analytical Method

| UPLC System: |
| --- |
| UPLC: Agilent 1290 |
| Detector 1: UV detector set at 267 nm |
| Detector 2: MSD XT in Positive Scan Mode |

| UPLC Conditions: |
| --- |
| Auto sampler temp.: RT |
| Column: ACE Avanor C18-PVP (100 x 2.1 mm; 1.7 μm) |
| Column temp: 40° C. |
| Gradient: |
| Mobile phase A: 0.7 gram ammonium formate 0.1% formic acid in water |
| Mobile phase B: 0.1% formic acid in methanol |
| Flow: 0.27 mL/min |
| Run time: 25 minutes |

| Gradient: | Time [min]: | Eluent A: | Eluent B: |
| --- | --- | --- | --- |
| | 0 | 95% | 5% |
| | 4 | 95% | 5% |
| | 16.5 | 30% | 70% |
| | 20 | 30% | 70% |
| | 20.1 | 95% | 5% |
| | 25 | 95% | 5% |

| Sample preparation: | |
| --- | --- |
| Concentration: | ca. 1.0 mg/mL |
| Solvent: | Water: Acetonitrile (60:40 v/v) + 0.1% formic acid |
| Injection volume: | 1 μl |

Figure 17:
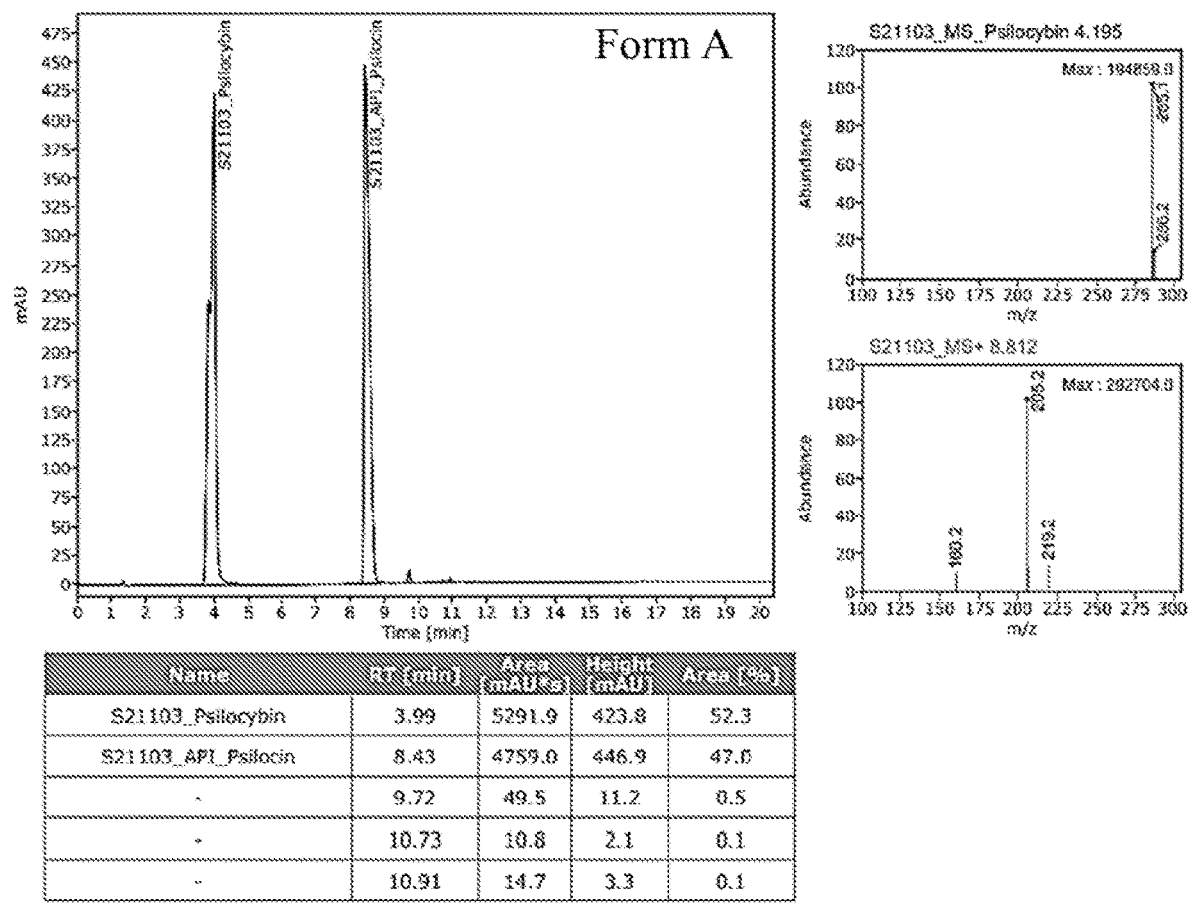
FIG. 17 shows the HPLC chromatogram of crystalline Form A.

Crystalline Form A: Reference solutions of the psilocin were made in concentrations of about 1 mg/ml. A solution of about 2 mg/mL of crystalline Form A was made in ACN/water 40/60% v/% v+0.01% formic acid. The stoichiometry (psilocybin:psilocin) of crystalline Form A was determined as 1:1. The HPLC chromatogram is shown in FIG. 17.

Figure 18:
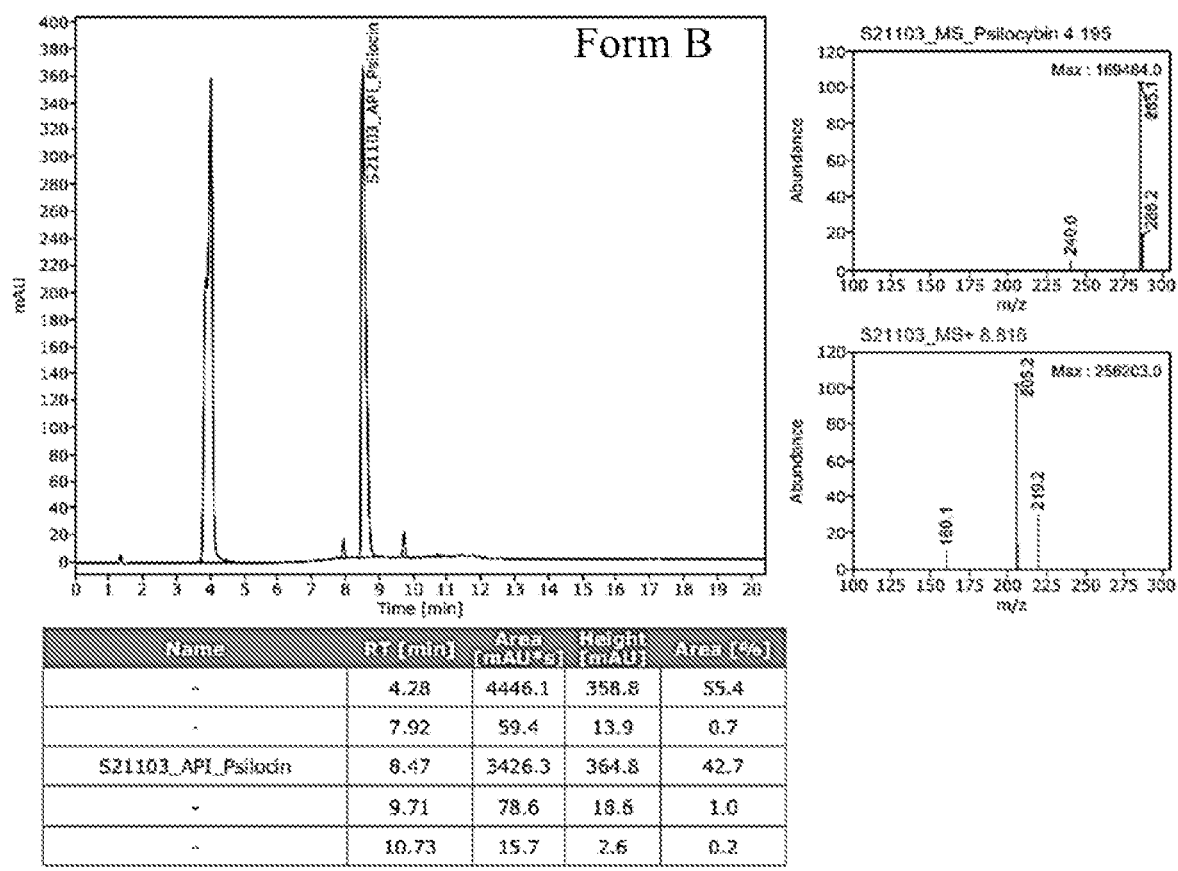
FIG. 18 shows the HPLC chromatogram of crystalline Form B.

Crystalline Form B: Reference solutions of the psilocin were made in concentrations of about 1 mg/ml. A solution of about 2 mg/mL of crystalline Form B was made in ACN/water 40/60% v/% v+0.01% formic acid. Applying the equation presented below (1), the stoichiometry (psilocybin:psilocin) of crystalline Form B was determined as 1.3:1. The HPLC chromatogram is shown in FIG. 18.

Figure 19:
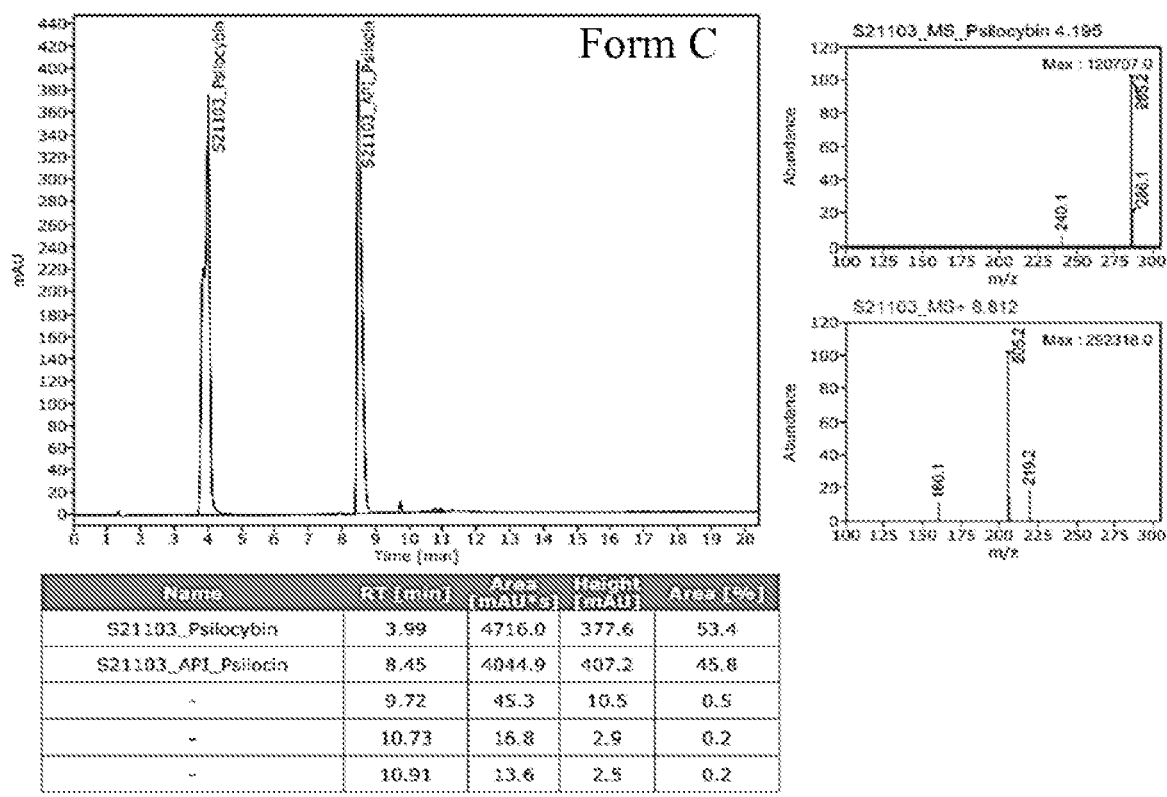
FIG. 19 shows the HPLC chromatogram of crystalline Form C.

Crystalline Form C: Reference solutions of the psilocin were made in concentrations of about 1 mg/ml. A solution of about 2 mg/mL of crystalline Form C was made in ACN/water 40/60% v/% v+0.01% formic acid. The stoichiometry (psilocybin:psilocin) of crystalline Form C was determined as 1:1. The HPLC chromatogram is shown in FIG. 19.

Example 7

Crystal Structure

High Resolution X-Ray Powder Diffraction (HR-XRPD): The HR-XRPD data of crystalline Form A were collected on D8 Advance diffractometer using Cu Kα1 radiation (1.54056 Å) with germanium monochromator at RT. Diffraction data were collected in the 2θ range 2.15-41.5°. Detector scan on solid state LynxEye detector was performed using 0.0157° per step with 5 sec/step scan speed. The samples were measured in 8 mm long glass capillary with 0.3 mm outer diameter. Before transferring into the capillary the analyzed solids (from Example 1 Exp ID TCS2) was grounded in agate mortar till all of the visible crystals disappeared and material became fine powder.

Cell parameters as well as crystal system were obtained using LSI-Index indexing program. The space group was selected on reflections condition and density of the crystal. The cell parameters, purity as well as instrument parameters were refined using Whole Powder Pattern Decomposition method.

The structure was solved using simulated annealing techniques as implemented in TOPAS6. For both components Psilocin and Psilocybin the Z_Matrix model was created using cif files from Cambridge Structural Data Base, CCDC1238288 for Psilocin and CCDC2128419 for Psilocybin.

Rietveld refinement was carried out using TOPAS6 (Bruker, 2017). All bond distances and angles were fixed and except for following torsion angles (C6-O5-P4-O2; C16-C15-C13-C14; C25-C24-N23-C22; C26-C25-C24-N23) only the rotation and translation of the molecules were allowed.

The following criteria of fit were used:
Yo,m and Yc,m are the observed and calculated data, respectively at data point m
M the number of data points
P the number of parameters
wm the weighting given to data point m which for counting statistics is given by wm=1/σ(Yo,m)2 where σ(Yo,m) is the error in Yo,m $$R_{exp} = \sqrt{\frac{M-P}{\sum w_m Y_{o,m}^2}} ; R_{wp} = \sqrt{\frac{\sum w_m(Y_{o,m}-Y_{c,m})^2}{\sum w_m Y_{o,m}^2}} ;$$

$$R_p = \sqrt{\frac{\sum |Y_{o,m}-Y_{c,m}|}{\sum Y_{o,m}}}$$

$$GOF = chi^2 = \frac{R_{wp}}{R_{exp}} = \sqrt{\frac{\sum w_m(Y_{o,m}-Y_{c,m})^2}{M-P}}$$

The structure was determined using simulated annealing method with the rigid body allowing both molecules free rotate and translate within a unit cell. Additionally, torsion angles of phosphate as well as both amine groups were treated as variables. After obtaining chemically reasonable solution, the model was refined using Rietveld algorithm.

Crystalline Form A crystallizes in orthorhombic primitive space group based on the reflections conditions and the final results of simulated annealing P212121 space group was chosen. Table 6 presents final crystal and refinement data for chosen model.

TABLE 6

Crystal data and final Rietveld parameters for solid for Psilocin-Psilocybin polymorph crystalline Form A.

| T [K] | 296(2) |
|---|---|
| λ[Å] | 1.54056 |
| Crystal system | Orthorhombic |
| Space group | $P2_12_12_1$ |

Unit Cell Dimensions

| a[Å] | 9.3674(3) |
|---|---|
| b[Å] | 11.2660(6) |
| c[Å] | 24.2741(9) |
| V[Å3] | 2561.7(2) |
| Z (Z') | 4(1) |
| Dc [g/cm3] | 1.267 |
| Cap. size [mm2] | 0.5 × 8 |
| 2θ Step size [°] | 0.016 |
| No of steps | 2503 |
| Time per step [s] | 17 |
| 2θ range [°] | 2.15 → 41.5 |
| Rexp | 3.31 |
| Rwp | 4.11 |
| Rp | 2.85 |
| GOF | 1.24 |
| RBrag | 1.95 |
| Impurities, other forms [%] | Below detection limit |

Figure 20:
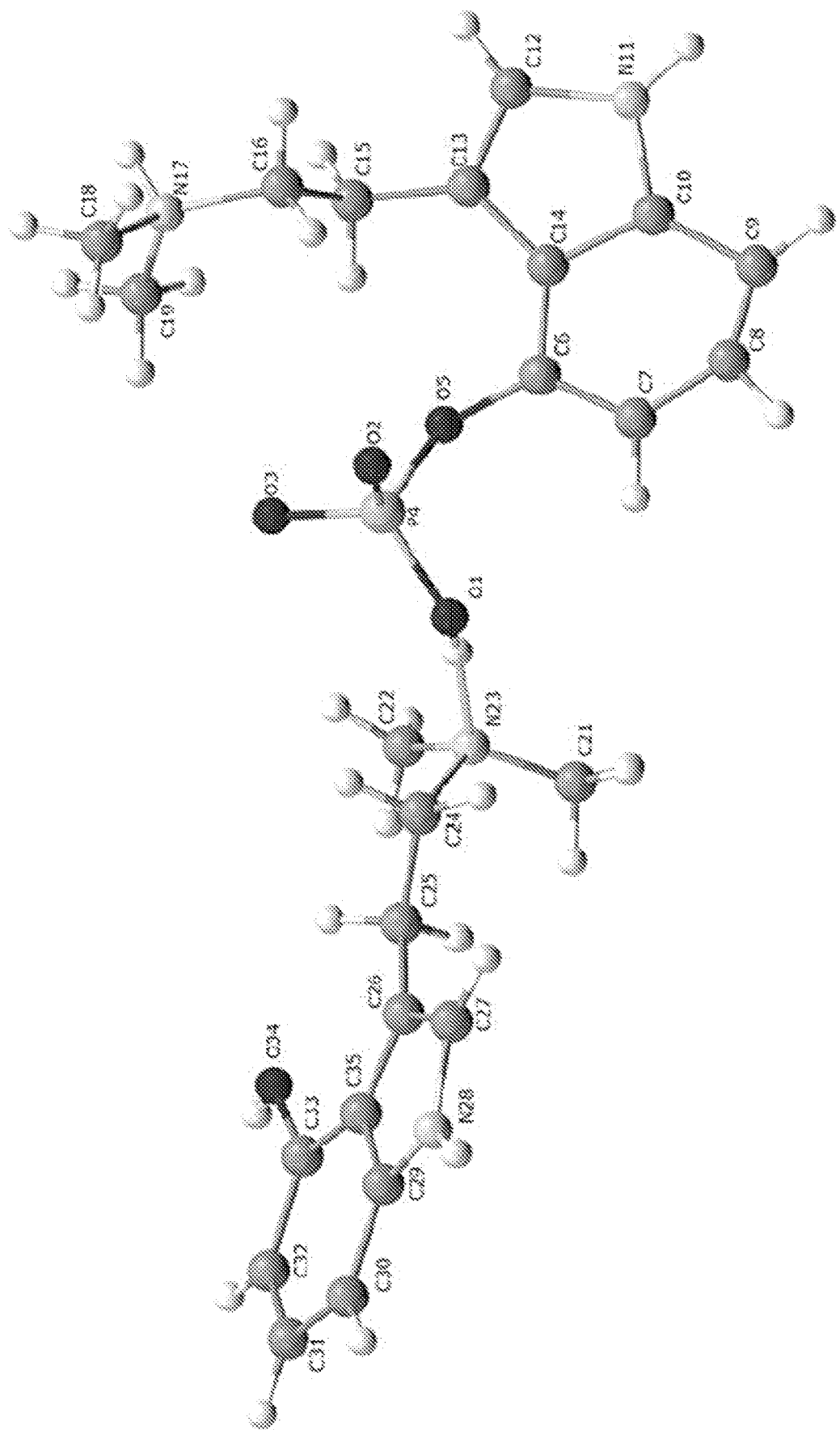
FIG. 20 shows the molecular structure and atom numbering scheme for Psilocin-Psilocybin pair obtained from simulated annealing based on the powder diffraction data of crystalline Form A.

The solution revealed that there is one Psilocin-Psilocybin pair in the asymmetric unit with no additional solvent or API molecules. All x, y, z positions of atoms can be found. FIG. 20 presents molecular structure of Psilocin-Psilocybin in crystalline Form A. As it can be seen the phosphate group of Psilocybin directly interacts with N amine atom from the Psilocin. The crystal is held by extensive network of intermolecular hydrogen bonds in which every non protonated O or N atom serves as an acceptor, while every N—H and O—H acts as a donor. Table 7 presents geometry of all hydrogen bonds found in the analyzed crystal.

TABLE 7

Hydrogen bonds found in the crystal of Psilocin-Psilocybin in crystalline Form A

| D-H...A | D-H [Å] | H...A [Å] | D...A [Å] | D-H...A [°] |
|---|---|---|---|---|
| O1-H1...N23[i] | 0.88(2) | 1.60(2) | 2.46(2) | 162(2) |
| N11-H11...O3[ii] | 0.96(5) | 2.17(4) | 2.97(4) | 140(6) |
| N17-H17...O2[iii] | 0.85(7) | 1.83(7) | 2.59(6) | 147(8) |
| N28-H28...O1[iv] | 0.87(7) | 2.32(6) | 3.13(5) | 153(10) |
| O34-H34...O3[v] | 0.88(10) | 1.69(8) | 2.49(7) | 151(5) |

Figure 21:
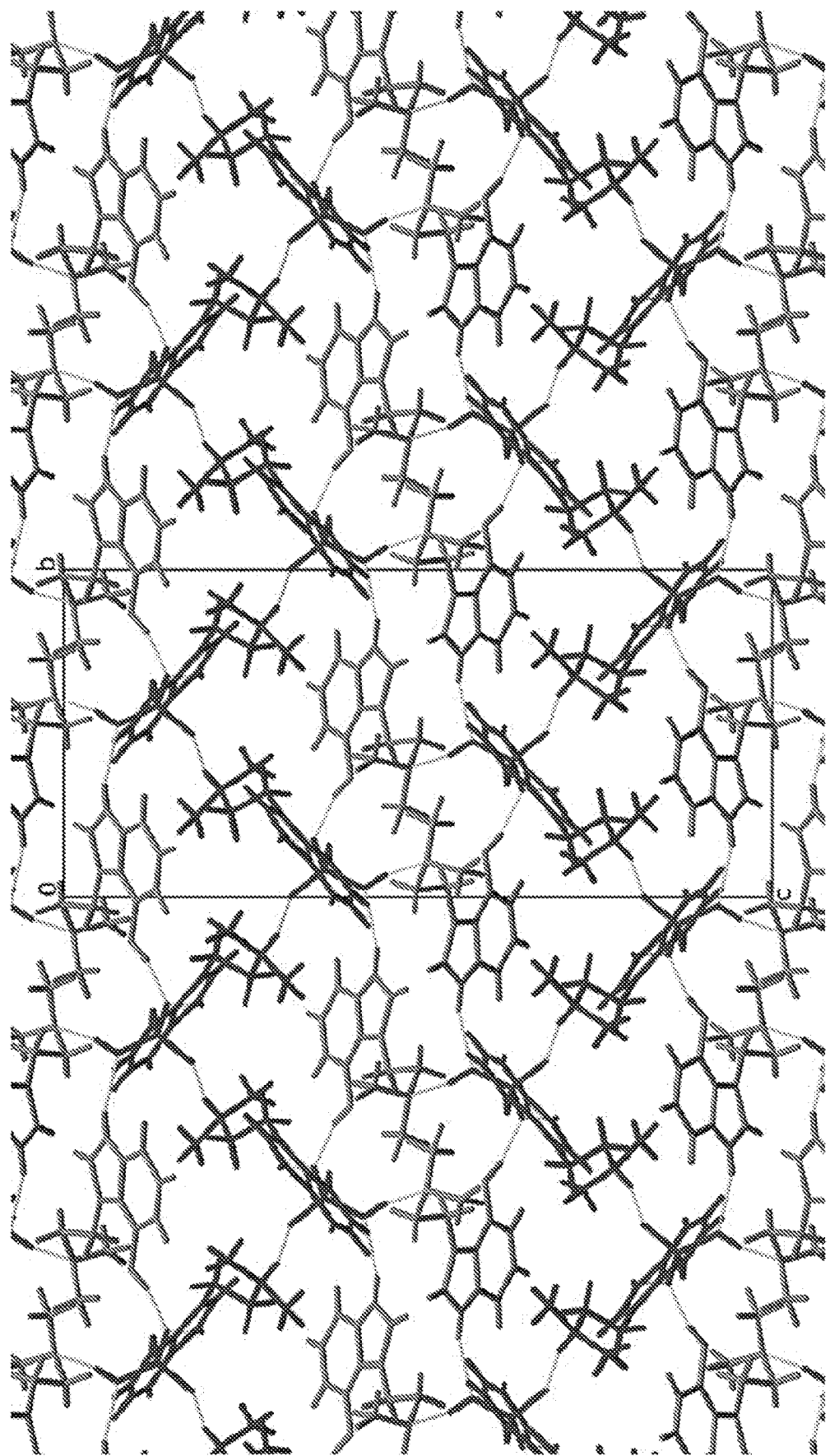
FIG. 21 shows the crystal packing and H-Bonds scheme in crystal of crystalline Form A along direction [1 0 0].

Symmetry transformations: [i]1 − x, y − 0.5, 1.5 − z; [ii]x − 1, y, z; [iii]−x, 0.5 + y, 0.5 − z; [iv]0.5 − x, −y, 0.5 + z; [v]0.5 − x, 1 − y, 0.5 + z The hydrogen bonds network of crystalline Form A forms a layered structure with the alternate layers built from Psilocin and Psilocybin molecules. These layers are parallel to the ab plane as it is presented in FIG. 21.

Atomic coordinates and equivalent isotropic displacement parameters ($Å^{2x} 10^3$) for non-hydrogen atoms of Form A are shown in Table 8. U(eq) is defined as one third of the trace of the orthogonalized $U^{ij}$ tensor.

TABLE 8

| | x | y | z | U(eq) |
|---|---|---|---|---|
| O1 | 0.1251(14) | 0.0326(16) | 0.4198(4) | 0.0253 |
| O2 | 0.077(3) | 0.0094(13) | 0.3153(5) | 0.0253 |
| O3 | 0.190(3) | 0.190(2) | 0.3483(6) | 0.0253 |
| P4 | 0.0916(7) | 0.0915(7) | 0.3636(3) | 0.0253 |
| O5 | −0.054(2) | 0.157(3) | 0.3724(5) | 0.0253 |
| C6 | −0.1818(8) | 0.102(5) | 0.3771(8) | 0.0253 |
| C7 | −0.221(2) | 0.009(6) | 0.4089(13) | 0.0253 |
| C8 | −0.357(3) | −0.030(9) | 0.4084(19) | 0.0253 |
| C9 | −0.466(2) | 0.022(11) | 0.375(2) | 0.0253 |
| C10 | −0.4261(9) | 0.116(10) | 0.3436(15) | 0.0253 |
| N11 | −0.512(3) | 0.188(12) | 0.3068(16) | 0.0253 |
| C12 | −0.386(5) | 0.277(10) | 0.2836(13) | 0.0253 |
| C13 | −0.265(4) | 0.250(7) | 0.3069(10) | 0.0253 |
| C14 | −0.2791(18) | 0.156(7) | 0.3445(10) | 0.0253 |
| C15 | −0.139(6) | 0.313(5) | 0.2890(13) | 0.0253 |
| C16 | −0.082(4) | 0.261(6) | 0.2343(10) | 0.0253 |
| N17 | 0.054(6) | 0.324(5) | 0.2219(15) | 0.0253 |
| C18 | 0.140(5) | 0.246(6) | 0.1809(13) | 0.0253 |
| C19 | 0.146(7) | 0.370(3) | 0.269(2) | 0.0253 |
| C21 | 0.8842(18) | 0.5884(19) | 0.9383(6) | 0.0253 |
| C22 | 0.7490(17) | 0.7295(10) | 0.9827(10) | 0.0253 |
| N23 | 0.8087(12) | 0.6116(8) | 0.9893(5) | 0.0253 |
| C24 | 0.7012(15) | 0.5244(13) | 1.0037(8) | 0.0253 |
| C25 | 0.591(2) | 0.533(3) | 0.9591(11) | 0.0253 |
| C26 | 0.508(4) | 0.422(3) | 0.9490(17) | 0.0253 |
| C27 | 0.543(5) | 0.306(3) | 0.963(2) | 0.0253 |
| N28 | 0.435(7) | 0.236(4) | 0.942(3) | 0.0253 |
| C29 | 0.337(7) | 0.302(6) | 0.917(3) | 0.0253 |
| C30 | 0.212(8) | 0.268(7) | 0.891(3) | 0.0253 |
| C31 | 0.124(7) | 0.356(9) | 0.868(3) | 0.0253 |
| C32 | 0.161(6) | 0.474(8) | 0.872(3) | 0.0253 |
| C33 | 0.292(5) | 0.508(6) | 0.899(3) | 0.0253 |
| O34 | 0.330(4) | 0.628(6) | 0.906(3) | 0.0253 |
| C35 | 0.379(5) | 0.422(5) | 0.920(2) | 0.0253 |

Hydrogen coordinates and isotropic displacement parameters ($Å^{2x} 10^3$) of Form A are shown in Table 9. U(eq) is defined as one third of the trace of the orthogonalized $U^{ij}$ tensor.

TABLE 9

| | x | y | z | U(eq) |
|---|---|---|---|---|
| H1 | 0.1396(11) | 0.074(2) | 0.4502(3) | 0.0253 |
| H7 | −0.151(3) | −0.029(5) | 0.4319(14) | 0.0253 |
| H8 | −0.379(5) | −0.097(9) | 0.431(2) | 0.0253 |
| H9 | −0.563(3) | −0.005(13) | 0.374(2) | 0.0253 |
| H11 | −0.612(2) | 0.172(14) | 0.3030(19) | 0.0253 |
| H12 | −0.389(6) | 0.337(10) | 0.2556(15) | 0.0253 |
| H15A | −0.075(5) | 0.294(4) | 0.3185(12) | 0.0253 |
| H15B | −0.147(8) | 0.398(5) | 0.2858(18) | 0.0253 |
| H16A | −0.146(5) | 0.280(7) | 0.2048(11) | 0.0253 |
| H16B | −0.074(3) | 0.176(5) | 0.2375(8) | 0.0253 |
| H17 | 0.041(8) | 0.386(5) | 0.2026(19) | 0.0253 |
| H18A | 0.205(4) | 0.181(6) | 0.1844(12) | 0.0253 |
| H18B | 0.203(6) | 0.295(7) | 0.1601(17) | 0.0253 |
| H18C | 0.075(4) | 0.206(7) | 0.1563(10) | 0.0253 |
| H19A | 0.213(7) | 0.336(3) | 0.2941(19) | 0.0253 |
| H19B | 0.086(8) | 0.405(2) | 0.296(2) | 0.0253 |
| H19C | 0.211(9) | 0.429(4) | 0.255(2) | 0.0253 |
| H21A | 0.951(2) | 0.627(3) | 0.9141(7) | 0.0253 |
| H21B | 0.817(3) | 0.575(3) | 0.9093(5) | 0.0253 |
| H21C | 0.944(2) | 0.520(2) | 0.9427(10) | 0.0253 |
| H22A | 0.778(2) | 0.8072(10) | 0.9708(14) | 0.0253 |
| H22B | 0.715(2) | 0.7579(14) | 1.0176(12) | 0.0253 |
| H22C | 0.6710(17) | 0.7266(16) | 0.9571(11) | 0.0253 |
| H24A | 0.6599(17) | 0.542(2) | 1.0390(8) | 0.0253 |
| H24B | 0.742(2) | 0.4463(11) | 1.0054(11) | 0.0253 |
| H25A | 0.635(3) | 0.565(3) | 0.9267(9) | 0.0253 |
| H25B | 0.5179(14) | 0.587(3) | 0.9706(16) | 0.0253 |
| H27 | 0.629(5) | 0.2905(18) | 0.984(3) | 0.0253 |
| H28 | 0.436(8) | 0.159(4) | 0.946(4) | 0.0253 |
| H30 | 0.186(9) | 0.185(8) | 0.890(4) | 0.0253 |

TABLE 9-continued

|  | x | y | z | U(eq) |
|---|---|---|---|---|
| H31 | 0.037(8) | 0.334(10) | 0.851(4) | 0.0253 |
| H32 | 0.100(6) | 0.533(9) | 0.856(4) | 0.0253 |
| H34 | 0.294(4) | 0.682(7) | 0.884(3 | 0.0253 |

Figure 22:
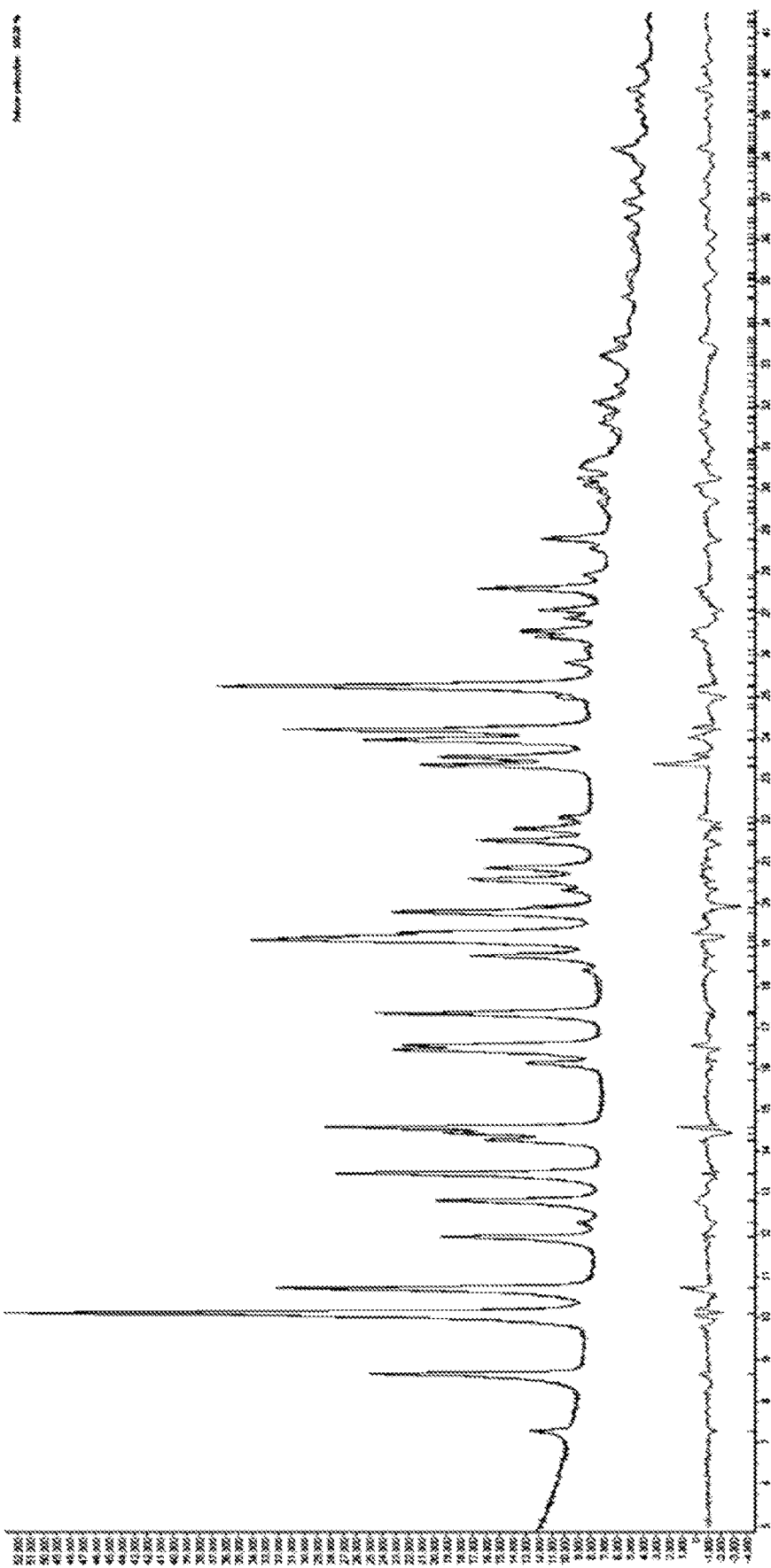
FIG. 22 shows the graphical representation of the final cycles of Rietveld refinement for crystalline Form A.

FIG. 22 shows the graphical representation of the final cycles of Rietveld refinement which confirms that the model fits very well with collected diffractogram for crystalline Form A.

Although the invention has been described with reference to the above examples, it will be understood that modifications and variations are encompassed within the spirit and scope of the invention. Accordingly, the invention is limited only by the following claims.

What is claimed is:

1. A composition comprising a crystalline form of psilocin and psilocybin:

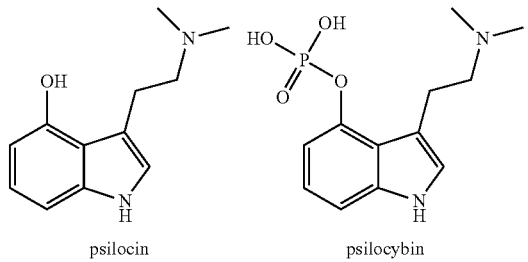

wherein the crystalline form is crystalline Form A;
wherein crystalline Form A is characterized by a XRPD pattern comprising a peak at a 2θ angle of 10.1° and 19.16°; and
wherein crystalline Form A is a co-crystal formed between psilocin and psilocybin.

2. The composition of claim 1, wherein the XRPD pattern further comprises a peak at a 2θ angles of 10.74°, 25.3°, and 24.07°.

3. The composition of claim 2, wherein the XRPD pattern further comprises a peak at a 2θ angles of 14.54°, 16.5°, 13.44°, 23.42°, and 8.62°.

4. The composition of claim 1, wherein crystalline Form A is characterized by a DSC plot comprising a sharp endothermic event at a temperature of about 255° C.

5. The composition of claim 1, wherein crystalline Form A has ratio of psilocybin to psilocin of about 1:1.

6. The composition of claim 1, wherein crystalline Form A has a chemical purity of about 95% or greater.

7. The composition of claim 1, wherein crystalline Form A contains not more than about 5 mol % of other solid forms.

8. The composition of claim 1, wherein crystalline Form A of psilocin and psilocybin comprises about 95 mol % crystalline Form A, about 2.5 mol % psilocin, and about 2.5 mol % psilocybin.

9. A pharmaceutical composition comprising a crystalline form of psilocin and psilocybin and a pharmaceutically acceptable excipient

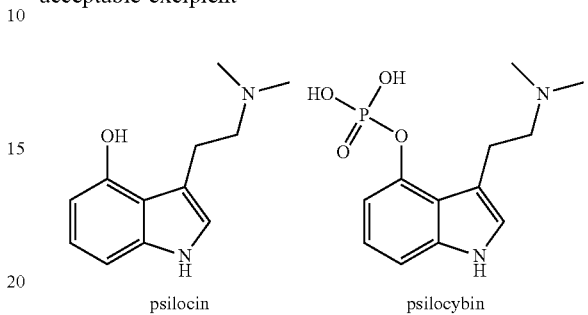

wherein the crystalline form is crystalline Form A;
wherein crystalline Form A is characterized by a XRPD pattern comprising a peak at a 2θ angle of 10.1° and 19.16°; and
wherein crystalline Form A is a co-crystal formed between psilocin and psilocybin.

10. The pharmaceutical composition of claim 9, wherein the XRPD pattern further comprises a peak at a 2θ angles of 10.74°, 25.3°, and 24.07°.

11. The pharmaceutical composition of claim 10, wherein the XRPD pattern further comprises a peak at a 2θ angles of 14.54°, 16.5°, 13.44°, 23.42°, and 8.62°.

12. The pharmaceutical composition of claim 9, wherein crystalline Form A is characterized by a DSC plot comprising a sharp endothermic event at a temperature of about 255° C.

13. The pharmaceutical composition of claim 9, wherein crystalline Form A has ratio of psilocybin to psilocin of about 1:1.

14. The pharmaceutical composition of claim 9, wherein crystalline Form A has a chemical purity of about 95% or greater.

15. The pharmaceutical composition of claim 9, wherein crystalline Form A of psilocin and psilocybin comprises about 95 mol % crystalline Form A, about 2.5 mol % psilocin, and about 2.5 mol % psilocybin.

* * * * *